United States Patent
Voellmy

(10) Patent No.: US 7,279,565 B2
(45) Date of Patent: *Oct. 9, 2007

(54) MOLECULAR REGULATORY CIRCUITS TO ACHIEVE SUSTAINED ACTIVATION OF GENES OF INTEREST BY A SINGLE STRESS

(76) Inventor: Richard Voellmy, Avenue Des Cerisiers 39B, Pully, Vaud (CH) 1009

( * ) Notice: Subject to any disclaimer, the term of this patent is extended or adjusted under 35 U.S.C. 154(b) by 442 days.

This patent is subject to a terminal disclaimer.

(21) Appl. No.: 10/996,420

(22) Filed: Nov. 26, 2004

(65) Prior Publication Data

US 2005/0191659 A1 Sep. 1, 2005

Related U.S. Application Data

(63) Continuation-in-part of application No. 10/046,420, filed on Oct. 26, 2001, now Pat. No. 7,132,521, which is a continuation of application No. 09/304,121, filed on May 3, 1999, now Pat. No. 6,342,596.

(60) Provisional application No. 60/084,236, filed on May 5, 1998.

(51) Int. Cl.
 *C07H 21/02* (2006.01)
(52) U.S. Cl. ............... 536/23.1; 435/69.1; 435/235.1; 435/252.3; 435/320.1; 435/455; 536/23.4
(58) Field of Classification Search .................. None
See application file for complete search history.

(56) References Cited

U.S. PATENT DOCUMENTS 6,342,596 B1 * 1/2002 Voellmy .................... 536/24.1

7,132,521 B2 * 11/2006 Voellmy .................... 536/23.1

OTHER PUBLICATIONS

Ghazal P et al. Enhancement of RNA polymerase II initiation complexes by a novel DNA control domain downstream . . . J. Virology. May 1991. vol. 65 (5), pp. 2299-2307.
Jaeckle H et al. Transcriptional cascades in Drosophila. Current Opinion in Cell Biolog. Jun. 1993. vol. 5 (3), pp. 505-512. ISSN: 0955-0674.

* cited by examiner

*Primary Examiner*—Long V. Le
*Assistant Examiner*—Michelle Horning
(74) *Attorney, Agent, or Firm*—Richard Voellmy

(57) ABSTRACT

The exposure of cells, tissues and organs to "stress," such as elevated temperature, stimulates production of active heat stress transcription factors (HSF), which in turn, induce expression of genes regulated by stress promoters. Normally, the activity of stress promoters declines after cells, tissues and organs are returned to a normal condition. The present invention relates to molecular circuits that provide for sustained expression of a gene of interest subsequent to a single application of stress. Generally, the molecular circuits of the invention comprise (a) a first nucleic acid molecule that comprises a gene encoding a transcription factor and a first promoter or a combination promoter activatable by stress and by the transcription factor, wherein the first promoter or the combination promoter and the transcription factor gene are operably linked, and (b) a second nucleic acid molecule that comprises a gene of interest and a second promoter activatable by the transcription factor, wherein the second promoter and the gene of interest are operably linked.

16 Claims, 7 Drawing Sheets

Figure 5

MOLECULAR REGULATORY CIRCUITS TO ACHIEVE SUSTAINED ACTIVATION OF GENES OF INTEREST BY A SINGLE STRESS

RELATED APPLICATIONS

This application is a Continuation-in-Part of application Ser. No. 10/046,420, filed Oct. 26, 2001 now U.S. Pat. No. 7,132,521, which application is a Continuation of application Ser. No. 09/304,121, filed May 3, 1999, from which U.S. Pat. No. 6,342,596 issued, and that claimed priority from Provisional Application 60/084,236 filed May 5, 1998. The contents of U.S. Pat. No. 6,342,596 are incorporated herein in their entirety.

TECHNICAL FIELD

The present invention relates generally to methods for controlling expression of a foreign gene. In particular, the present invention relates to methods for inducing sustained gene expression by a single application of stress.

BACKGROUND OF THE INVENTION

Exposure of cells, tissues and organs to "stress," such as elevated temperature, heavy metals, oxidants, chemicals interfering with mitochondrial function, alcohols, hypoxia, hyperosmotic and hypoosmotic environments, amino acid analogues, and benzoquinone ansamycins results in the activation or enhanced activity of a group of genes known as heat shock or stress (hsp) genes. See, for example, Scharf et al., "Heat Stress Promoters and Transcription Factors," in Results and Problems in Cell Differentiation 20, Nover (Ed.), pages 125-162 (Springer-Verlag 1994). When cells, tissues and organs are returned to a normal condition, stress gene activity declines, until it reaches the low pre-stress level.

Stress genes encode a small number of heat shock or stress protein (Hsp) families. Major families of stress proteins are distinguished on the basis of molecular weight and amino acid sequence. See, for example, Nover and Scharf, Cell. Mol. Life Sci. 53:80 (1997). They include Hsp 110 (Hsp's with a subunit molecular weight of about 110 kDa), Hsp 104, Hsp90, Hsp70, Hsp60, Hsp27, Hsp10 and ubiquitin. Many of these Hsp's are molecular chaperones that participate in such basic cellular processes as protein folding, protein degradation and protein trafficking.

Promoter regions of stress genes typically include so-called heat shock element (HSE) sequences. These sequences are essential to render the genes activatable by stress. HSE provide binding sites of proteins named heat shock transcription factors (HSF). See, for example, Wu, "Heat Shock Transcription Factors: Structure and Regulation," in Annu. Rev. Cell Dev. Biol. 11:441 (1995); Nover and Scharf, Cell. Mol. Life Sci. 53:80 (1997). Mammalian cells can express at least three different HSF. It is thought that the factor termed HSF1 is responsible for the regulation of hsp genes by stress. HSF1 is continuously and ubiquitously expressed in mammalian cells. In the absence of stress, the factor is present in an inactive form, unable to bind HSE sequences of stress gene promoters and to enhance their transcription. During stress, HSF1 is activated, and in the activated form, binds HSE DNA and stimulates transcription of stress genes. Subsequent to a stressful event, the factor relatively rapidly returns to its inactive form. Consequently, transcription of stress genes ceases. Mutant forms of HSF1 have been constructed that are capable of constitutively transactivating stress genes, in the absence of stress.

Promoters of stress genes have been linked to genes of interest to render the genes activatable by stress. Constructs of this kind were used to prepare cell lines, in which genes of interest could be activated by heat or some other form of stress. For example, cell lines have been prepared that contain a stress gene promoter-controlled growth hormone gene. Dreano et al., Gene 49:1 (1986). Moreover, transgenic flies and transgenic nematodes have been produced that express a β-galactosidase gene under stress control. See, for example, Voellmy and Ananthan, U.S. Pat. No. 5,346,812, Candido and Jones, Trends Biotechnol. 14:125 (1996), and Jones et al., Toxicology 109:119 (1996).

A major drawback of the use of stress gene promoters, also referred to herein as stress promoters, to control regulation of a gene of interest is that gene expression induced by a stress promoter can be maintained beyond the duration of the stress treatment only under conditions of extreme stress. Yet such extreme conditions are incompatible with cell survival.

Therefore, a need exists for a means to take advantage of stress-induced gene regulation under conditions that do not endanger cell viability.

SUMMARY OF THE INVENTION

The present invention provides molecular circuits that can be activated by stress, and that regulate expression of a gene of interest.

In particular, the present invention provides molecular circuits comprising (a) a first nucleic acid molecule that comprises a gene encoding a transcription factor and a first promoter activatable by stress and by the transcription factor, wherein the first promoter and the transcription factor gene are operably linked, and (b) a second nucleic acid molecule that comprises a gene of interest and a second promoter activatable by the transcription factor, wherein the second promoter and the gene of interest are operably linked. In a variation of this type of molecular circuit, the molecular circuit comprises a gene of interest that encodes a transactivator, and the molecular circuit further comprises a nucleic acid molecule comprising a second gene of interest and a promoter activatable by the transactivator, wherein the second gene of interest and the transactivator-activatable promoter are operably linked. The molecular circuits may comprise two separate nucleic molecules, or the molecular circuits may comprise a single nucleic acid molecule that contains the first and second nucleic acid molecules.

The present invention also includes molecular circuits comprising (a) a first nucleic acid molecule that comprises a gene encoding a transcription factor and a first promoter activatable by stress, wherein the first promoter and the transcription factor gene are operably linked, (b) a second nucleic acid comprising a gene encoding the transcription factor and a second promoter activatable by the transcription factor, wherein the second promoter and the transcription factor gene are operably linked, and (c) a third nucleic acid molecule that comprises a gene of interest and a third promoter activatable by the transcription factor, wherein the third promoter and the gene of interest are operably linked. These molecular circuits may comprise (a) three separate nucleic acid molecules, (b) the third nucleic acid molecule and a single nucleic acid molecule that comprises the first nucleic acid molecule and the second nucleic acid molecule, or (c) a single nucleic acid molecule comprises the first nucleic acid molecule, the second nucleic acid molecule, and the third nucleic acid molecule.

The present invention further contemplates molecular circuits comprising (a) a first nucleic acid molecule that comprises a gene encoding a first transcription factor and a first promoter activatable by stress, wherein the first promoter and the first transcription factor gene are operably linked, (b) a second nucleic acid comprising a gene encoding a second transcription factor and a second promoter activatable by the first transcription factor and the second transcription factor, wherein the second promoter and the second transcription factor gene are operably linked, and (c) a third nucleic acid molecule that comprises a gene of interest and a third promoter activatable by the second transcription factor, wherein the third promoter and the gene of interest are operably linked. These molecular circuits may comprise (a) three separate nucleic acid molecules, (b) the third nucleic acid molecule and a single nucleic acid molecule that comprises the first nucleic acid molecule and the second nucleic acid molecule, or (c) a single nucleic acid molecule comprises the first nucleic acid molecule, the second nucleic acid molecule, and the third nucleic acid molecule.

The present invention also contemplates molecular circuits comprising (a) a first nucleic acid molecule that comprises a gene encoding a transcription factor and a first promoter activatable by stress, wherein the first promoter and the transcription factor gene are operably linked, and (b) a second nucleic acid molecule that comprises a gene of interest, the transcription factor gene, and a second promoter activatable by the transcription factor, wherein the second promoter is operably linked with the gene of interest and the transcription factor gene. These molecular circuits may comprise two nucleic molecules, or the molecular circuits may be contained within a single nucleic acid molecule that contains the first and second nucleic acid molecules.

In additional specific embodiments, the invention relates to molecular circuits that are delivered into a cell, comprising (a) a first nucleic acid comprising a gene encoding a transcription factor, the gene being operably linked to a combination promoter activatable by stress and by the transcription factor, the combination promoter comprising a nucleotide sequence including a stress promoter and an associated RNA leader sequence into which (RNA leader sequence) a promoter activatable by the transcription factor is inserted or a nucleotide sequence including a promoter activatable by the transcription factor and an associated RNA leader into which (RNA leader sequence) a stress promoter is inserted, and (b) a second nucleic acid comprising a gene of interest, the gene of interest being operably linked to a promoter activatable by the transcription factor. A molecular circuit of this kind may be present in single nucleic acid that comprises both first and second nucleic acids. Furthermore, the promoter that is operably linked to the gene of interest can also be a combination promoter activatable by stress and the transcription factor. Moreover, the gene encoding the transcription factor and the gene of interest can both be present on the same nucleic acid and be operably linked to a single combination promoter activatable by stress and the transcription factor. In a preferred molecular circuit in which a combination promoter controls expression of a gene encoding a transcription factor, the combination promoter comprises a nucleotide sequence including a stress promoter and an associated RNA leader sequence into which (RNA leader sequence) an intron sequence including a promoter activatable by the transcription factor is inserted or a nucleotide sequence including a promoter activatable by the transcription factor and an associated RNA leader into which (RNA leader sequence) an intron sequence including a stress promoter is inserted. In more preferred molecular circuits employing a combination promoter, the combination promoter comprises a nucleotide sequence from the human Hsp70B stress gene including a stress promoter and an RNA leader sequence into which an intron sequence including a promoter activatable by the transcription factor is inserted. It is noted that the above descriptions of combination promoters relate to their structure and not to steps involved in their construction. It is entirely immaterial whether a combination promoter was constructed by first insertion of an intron sequence into the RNA leader sequence associated with a first promoter and second insertion of a second promoter into the (inserted) intron sequence, or insertion of an intron sequence that already contained the second promoter. Specific examples of useful transcription factors to be used in molecular circuits of the invention, especially in molecular circuits employing a combination promoter, include EcR/RXR and a transcription factor comprising a GAL4 DNA-binding domain.

The invention also relates to nucleic acids comprising a gene encoding a transcription factor, the gene being operably linked to a combination promoter activatable by stress and by the transcription factor, the combination promoter comprising a nucleotide sequence including a stress promoter and an associated RNA leader sequence into which a promoter activatable by the transcription factor is inserted or a nucleotide sequence including a promoter activatable by the transcription factor and an associated RNA leader into which a stress promoter is inserted. A preferred combination promoter comprises a nucleotide sequence including a stress promoter and an associated RNA leader sequence into which an intron sequence including a promoter activatable by the transcription factor is inserted or a nucleotide sequence including a promoter activatable by the transcription factor and an associated RNA leader into which an intron sequence including a stress promoter is inserted. A more preferred combination promoter comprises a nucleotide sequence from the human Hsp70B stress gene including a stress promoter and an RNA leader sequence into which an intron sequence including a promoter activatable by the transcription factor is inserted.

Molecular circuits of the invention can also be used to control expression of host genes of interest. In this case, a molecular circuit is constituted in a host cell. Such a molecular circuit comprises (a) a nucleic acid delivered into the cell comprising a gene encoding a transcription factor, the gene being operably linked to a promoter or combination promoter activatable by stress and by the transcription factor, and (b) a gene of the host cell that is activatable by the transcription factor. In a different embodiment, the molecular circuit comprises (a) a nucleic acid delivered into the cell comprising a gene encoding a first transcription factor, the gene being operably linked to a promoter or combination promoter activatable by stress and by the first transcription factor, (b) a nucleic acid delivered into the cell comprising a gene for a second transcription factor, the gene being operably linked to a promoter activatable by the first transcription factor, and (c) a gene of the host cell that is activatable by the second transcription factor. The two nucleic acids delivered into the cell may be combined in a single nucleic acid. A further molecular circuit constituted in a host cell comprises (a) a nucleic acid delivered into the cell comprising a gene encoding a first transcription factor, the gene being operably linked to a stress promoter, (b) a nucleic acid delivered into the cell comprising a gene for a second transcription factor, the gene being operably linked to a promoter or combination promoter activatable by the first and second transcription factors, and (c) a gene of the host cell that is activatable by the second transcription factor. The two nucleic acids delivered into the cell may be combined in a single nucleic acid. Moreover, first and second transcription factors can be identical.

In molecular circuits of the present invention, the transcription factor can be a mutated heat shock transcription factor (HSF), a constitutively active transcription factor, or a transcription factor activated by a second stimulus other than a stress, e.g., by a small-molecule ligand. A suitable mutated HSF can be derived from a vertebrate HSF or from an insect HSF. For example, a suitable vertebrate HSF can be a mammalian HSF or an avian HSF.

The molecular circuits described herein can be contained within a single expression vector. Alternatively, molecular circuit nucleic acid molecules can be contained within a set of expression vectors, wherein each expression vector contains one or two molecular circuit nucleic acid molecules.

The present invention also contemplates recombinant host cells that comprise a molecular circuit. The molecular circuit may have the form of a single expression vector or an expression vector set, as described above. Suitable eukaryotic host cells include insect cells, avian cells, yeast cells, and mammalian cells.

The present invention further contemplates methods of producing a protein of interest, comprising the steps of: (a) culturing such recombinant host cells, (b) stimulating the first promoter by exposing the cultured recombinant cells to stress, and (c) isolating the protein of interest from the cultured recombinant host cells, wherein the protein of interest is expressed by the gene of interest. Step (b) can be achieved, for example, by heating the recombinant host cells.

The present invention also contemplates viruses that comprise an expression vector described above. Suitable viruses include adeno-associated viruses, adenoviruses, Herpes simplex viruses, alphaviruses, and pox viruses.

The present invention also includes pharmaceutical compositions that comprise a pharmaceutically acceptable carrier and either an expression vector or an expression vector set, as described above. Alternatively, a pharmaceutical composition of the present invention may comprise a pharmaceutically acceptable carrier and a virus, as described above.

The present invention further contemplates methods of treating a subject with a protein of interest, comprising the steps of: (a) administering to a subject a pharmaceutical composition described above, and (b) applying heat to the area of the subject in need of the protein of interest, wherein the heat treatment results in the stimulation of the expression of the gene of interest.

The present invention also includes methods of stimulating the expression of a gene of interest in a recombinant cell, comprising the steps of: (a) producing a recombinant host cell by introducing into a host cell either the expression vector, or an expression vector set, as described above, and (b) exposing the recombinant host cell to a condition of stress, wherein the stress exposure stimulates the first promoter to increase expression of the gene operably linked to the first promoter, which in turn, results in the stimulation of expression of the gene of interest.

These and other aspects of the present invention will become evident upon reference to the following detailed description and attached drawings. In addition, various references are identified below and are incorporated by reference in their entirety.

BRIEF DESCRIPTION OF THE DRAWINGS

Figure 5:
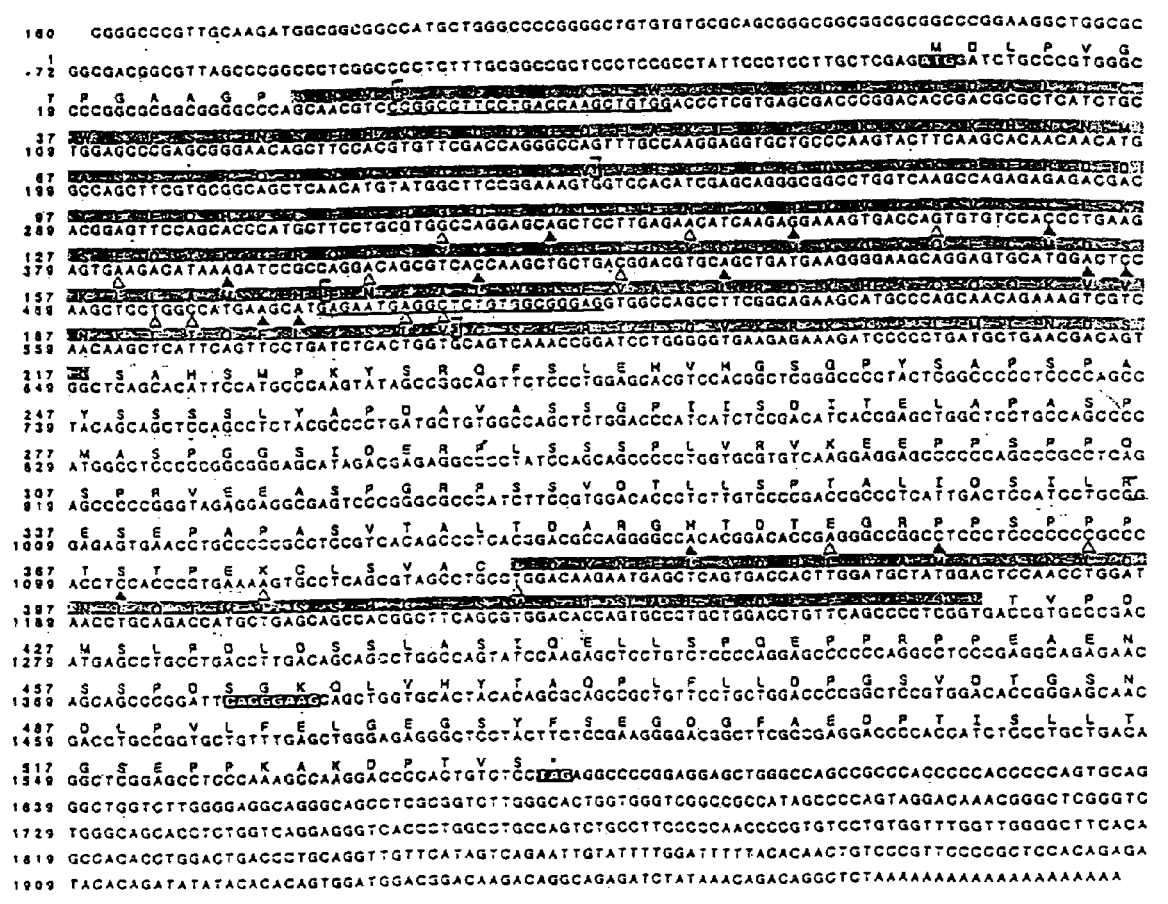

FIG. 5 shows the nucleotide and amino acid sequences of the human heat shock transcription factor HSF1 (SEQ ID NOs: 1 and 2, respectively).

DETAILED DESCRIPTION OF THE INVENTION

1. Definitions

Figure 1:
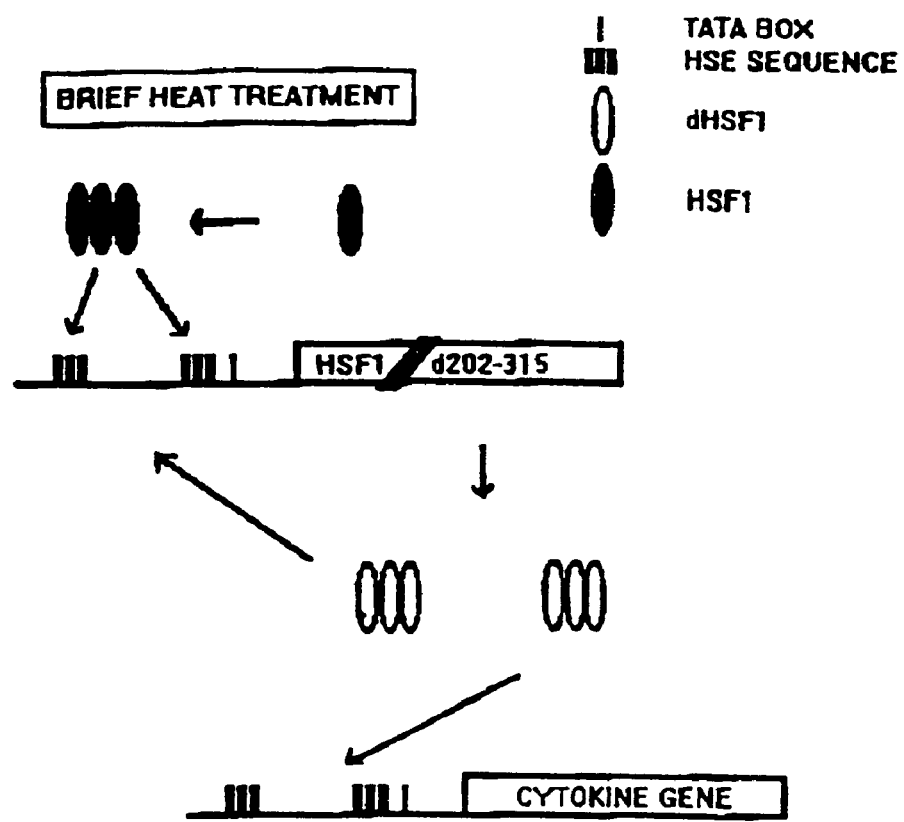
FIG. 1 is a schematic of the elements of a type 1 regulatory circuit and shows the interactions between the elements. "HSE" refers to heat shock element sequences that are binding sites of heat shock transcription factor (HSF) contained in typical hsp gene promoters. A "dHSF" is a constitutively active heat shock transcription factor that has been mutated to remove an element that represses the transcriptional ability of the factor.

In the description that follows, a number of terms are used extensively. The following definitions are provided to facilitate understanding of the invention.

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

As used herein, the term "immunomodulator" includes cytokines, stem cell growth factors, lymphotoxins, co-stimulatory molecules, hematopoietic factors, and synthetic analogs of these molecules.

An "isolated nucleic acid molecule" is a nucleic acid molecule that is not integrated in the genomic DNA of an organism. For example, a DNA molecule that encodes an immunomodulator that has been separated from the genomic DNA of a cell is an isolated DNA molecule. Another example of an isolated nucleic acid molecule is a chemically-synthesized nucleic acid molecule that is not integrated in the genome of an organism.

An "isolated polypeptide" is a polypeptide that is essentially free from contaminating cellular components, such as carbohydrate, lipid, or other proteinaceous impurities associated with the polypeptide in nature. That a particular protein preparation contains an isolated polypeptide can be shown by the appearance of a single band following sodium dodecyl sulfate (SDS)-polyacrylamide gel electrophoresis of the protein preparation and Coomassie Brilliant Blue staining of the gel.

A "promoter" is a nucleotide sequence that directs the transcription of a structural gene. Typically, a promoter is located in the 5' region of a gene, proximal to the transcriptional start site of a structural gene. However, a promoter may also include sequence elements in the transcribed region. Hence, the term "promoter" is often understood to include part or all of the RNA leader sequence of the associated gene. If a promoter is an inducible promoter, then the rate of transcription increases in response to an inducing agent. In contrast, the rate of transcription is not regulated by an inducing agent if the promoter is a constitutive promoter.

A "regulatory element" is a nucleotide sequence that modulates the activity of a promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

As used herein, a "transcription factor" is a protein that binds to a nucleic acid and thereby influences its transcription by altering rates of transcription initiation or elongation.

A "transactivator" is a transcription factor that enhances transcription initiation or elongation.

As used herein, a "chimeric transcription factor" is a protein comprising a DNA binding domain of one protein and a transcriptional activation domain of another protein. For example, a chimeric transcription factor may comprise a LexA DNA binding domain and a heat shock transcription factor activation domain.

In the case of a monomeric or homooligomeric transcription factor, the term "transcription factor gene" refers to the sequence coding for the factor polypeptide, supplemented with appropriate control elements that ensure proper termination of transcription, processing of RNA product, and translation. In the circuits described herein, the transcription factor gene is operably linked to a promoter activatable by stress and/or the transcription factor. In the case of heterooligomeric transcription factors, the term "transcription factor gene" refers to coding sequences required for the synthesis of all subunits, each supplemented with control elements, as described above. To construct the circuits of the kind described herein, at least one of the sequences encoding a subunit of a heterooligomeric transcription factor needs to be linked to an appropriately regulatable promoter (e.g., activatable by stress and/or the transcription factor). The promoter-linked sequences may be present in a single nucleic acid or may be in separate nucleic acids. Alternatively, the sequences may be arranged in tandem, separated by internal ribosome binding sites, and the entire arrangement of sequences may be linked to a single promoter.

A "heterodimeric transcription factor" is a transcription factor consisting of two different subunit polypeptides. An example of a heterodimeric transcription factor is the ecdysone receptor-retinoic acid receptor molecule described herein.

A "heat shock element (HSE)" is a nucleic acid sequence that binds with a heat shock transcription factor (HSF) to stimulate gene expression. HSEs are short, double-stranded nucleotide sequences whose minimal structure is 5' NGAANNTTCNNGAAN (SEQ ID NO: 3). See also, for example, Scharf et al., "Heat Stress Promoters and Transcription Factors," in Results and Problems in Cell Differentiation 20, Nover (Ed.), pages 125-162 (Springer-Verlag 1994).

A "stress gene promoter" or "stress promoter" can be a natural promoter of an isolated heat shock or stress (protein) gene whose transcription in its host cell is stimulated by stress, e.g., heat. Such a promoter contains one or more HSEs. A "stress gene promoter" or "stress promoter" as used herein can also be derived from a natural promoter of a stress gene by deletion of sequence elements not related to stress regulation or by insertion of additional sequence elements, especially additional HSE sequences. It may also be constructed by adding HSE sequences to a basal promoter, i.e., a promoter having all other sequence elements required for initiation and elongation of transcription by RNA polymerase II.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides. The regulatory circuits described herein can be used to stimulate expression of a gene of interest to produce a protein of interest. Regulatory circuits can also be used to control the expression of an anti-sense gene, a ribozyme gene, a gene encoding an inhibitory RNA (RNAi) or an external guide sequence gene in which genes a nucleic acid, rather than a protein, is the relevant end product.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, gene expression is placed under the control of a promoter. Such a gene is said to be "operably linked to" the promoter.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

In recombinant constructs described below, a regulatory element or a promoter controls the expression of a gene that is not associated with the regulatory element or promoter in nature. Such a construct is said to comprise a regulatory element or promoter and a "foreign gene." For example, a nucleic acid molecule comprising a promoter activatable by a heat shock transcription factor operably linked to a cytokine gene contains a cytokine gene as the foreign gene. The foreign gene is a type of "gene of interest," and the product of a foreign gene is a "foreign protein," which is a type of "protein of interest."

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

As used herein, a "gene of interest" is a gene encoding an RNA product or a polypeptide product.

"RNA leader region" of a gene refers to the transcribed but not translated sequence of the gene that begins at the start of transcription site and ends at the nucleotide preceding the translation initiation codon.

"Combination promoter" refers to an arrangement comprising a first promoter and an associated RNA leader region and a second promoter, wherein the second promoter is placed within the RNA leader region associated with the first promoter. It is noted that the second promoter may include both nontranscribed and transcribed sequences as described under "promoter". The second promoter may also be inserted embedded in an intron sequence.

2. Construction of a Type 1 Circuit

Several regulatory circuits are described herein that have the general feature that their use permits sustained activation of expression of a gene of interest by a single application of stress. Gene activity regulated by these circuits does not subside subsequent to the activating stress.

The most simple circuit consists of two elements: (1) a gene of interest functionally linked to a stress gene promoter, and (2) a gene encoding a constitutively activated mutated heat shock transcription factor (HSF), which is also functionally linked to a stress gene promoter. An example of a type 1 circuit is illustrated in FIG. 1. The two elements may be delivered into cells as a single nucleic acid or as separate nucleic acids. In the cells, both genes are either silent or expressed at appropriately low levels in the absence of stress. When the cells are stressed, promoters in both elements are activated by endogenous HSF, which results in the expression and accumulation of the gene product of interest and of mutated HSF. Mutated HSF continues to activate transcription of both the gene of interest and its own gene, resulting in the synthesis of more product of interest and mutated HSF. This cycle continues even if the cells are no longer under stress. Consequently, the gene of interest will remain active for an extended period or, possibly, until such time at which the cell has exhausted its capacity to transcribe and translate nucleic acids. Thus, this two-element system has the desired feature of permitting the sustained activation by stress of a gene of interest by a single stress.

When preparing the elements of the circuit, a number of factors need to be considered. First, the stress promoter controlling the expression of mutated HSF preferably should be tightly stress-regulated. Leaky expression from the promoter may result in accumulation of an amount of mutated HSF that is sufficient to stimulate expression from the promoter, resulting in gradually increased levels of HSF and ultimately in the full activation of the gene of interest. An example of a tightly regulated stress promoter is the promoter regulating the expression of the human hsp70B gene. Voellmy et al., Proc. Natl. Acad. Sci. USA 82:4949 (1985).

In addition to the choice of promoter, the level of basal expression of mutated HSF can be reduced by other manipulations well known in the art. For example, the half-life of the mRNA encoding mutated HSF can be reduced by including elements enhancing mRNA degradation in the 3' nontranslated sequence. Chen and Shyu, Trends Biochem. Sci. 20:465 (1995). It is also possible to reduce the rate of translation by introducing palindromic sequences of suitable length in the 5' nontranslated sequence of the mutated HSF1 gene (see Muhlrad et al., Mol. Cell. Biol. 15:2145 (1995), and references cited therein) or by altering the sequence of the region that includes the translation initiation codon. The stability of mutated HSF1 can also be reduced by insertion of residues, deletion of sequence elements that confer structural stability, or introduction of protease cleavage sites. The operation of the circuit and effects of manipulations of the type described above can be assessed by construction of a test circuit and analysis of its performance, as described below.

A stress-regulated test circuit is described in Example 1. Briefly, a first construct can be prepared by inserting into a suitable plasmid vector a fragment containing the human hsp70B promoter and a fragment containing the entire coding sequence of firefly luciferase such that the stress promoter controls expression of the luciferase sequence. A second plasmid vector can be constructed that contains a stress promoter linked to a gene encoding a mutated HSF, for example HSF1d202-316, or a derivative containing one or more of the modifications discussed before to reduce level of accumulation. These constructs are prepared using routine subcloning procedures well known in the art. The constructs are then co-transfected into a suitable cell such as, for example, human HeLa cells, using a standard technique, such as calcium phosphate transfection, liposome-mediated transfection, electroporation, using viral vectors, and the like. Techniques for introducing vectors into eukaryotic cells are described, for example, by Ausubel et al. (eds.), Short Protocols in Molecular Biology, 3rd Edition, (John Wiley & Sons, Inc. 1995), and by Murray (ed.), Gene Transfer and Expression Protocols (Humana Press 1991).

Control cells are singly transfected with the stress promoter-luciferase construct. Transfection efficiency may be estimated by co-transfection of a suitable reporter gene such as, for example, a gene expressing constitutively a green fluorescent protein that can be readily monitored by cytometry. One day after transfection, one of every two parallel cultures is briefly heat-treated (one hour at 42-44° C. in the case of HeLa cells) and then incubated at normal temperature (37° C. in the case of HeLa cells) for another two days. Cells are then harvested, and luciferase activity assays are carried out.

No luciferase activity will be measured in cells singly transfected with the stress promoter-luciferase construct that had not been heat-treated, and only low levels of activity will be detected in heat-treated cells. Luciferase and its mRNA are relatively unstable in mammalian cells. Although expressed at a high level during and immediately following heat treatment, synthesis declines after heat treatment, and after two days only little of the enzyme initially synthesized is still present. If the circuit is functional, cells that have not been heat-treated but have been co-transfected with both constructs will have low to undetectable luciferase activity, whereas heat-treated, co-transfected cells will have levels of luciferase that are many times higher than those measured in singly transfected cells. High levels of luciferase are present in the heat-treated, co-transfected cells because mutated HSF1 is expressed and maintained, and the factor continuously stimulates expression from the luciferase gene. If levels of luciferase are unacceptably elevated in not-heat-treated, co-transfected cells, some of the manipulations described before to reduce levels of mutated HSF1 can be carried out, and their effects assessed in the test system.

Any stress promoter may be used in the circuit. A stress promoter as used herein is defined as a promoter of a known stress-regulated gene, a promoter derived from that of a known stress-regulated gene, or a promoter assembled by addition of HSE sequences in a basal promoter. Typically such stress promoters contain one or several HSE sequences. HSEs are short, double-stranded nucleotide sequences whose minimal structure is 5' NGAANNTTCNNGAAN. Related sequence elements can also function as HSEs. Amin et al., Mol. Cell. Biol. 8:3761 (1988). The functionality of a putative HSE can be tested by introducing it as one or several copies upstream from a basal promoter that is functionally linked to a convenient reporter gene. Amin et al., Mol. Cell. Biol. 7:1055 (1987). The resulting constructs are tested by introduction into a cell of choice and analysis of their activity in the stressed (e.g., heat-treated) and not-stressed cells.

Examples of suitable stress-inducible promoters of known stress genes include vertebrate and insect hsp promoters. Preferred vertebrate hsp promoters include hsp90α, hsp70, and hsp25-27 promoters. An example of a preferred human promoter is the human hsp70B promoter. Additional suitable stress promoters are known to those of skill in the art. See, for example, Nover, Enzyme Microb. Technol. 9:130 (1987), Nover, Heat Shock Response (CRC Press, Inc. 1991), Gunther and Walter, Experientia 50:987 (1994), Craig et al., Cold Spring Harbor Symposia on Quantitative Biology 60:441 (1995), Scharf et al., "Heat Stress Promoters and Transcription Factors," in Results and Problems in Cell Differentiation 20, Nover (Ed.), pages 125-162 (Springer-Verlag 1994), Voellmy, Crit. Rev. Eukaryotic Gene Expr. 4:357 (1994), and Nover and Scharf, Cell. Mol. Life Sci. 53:80 (1997).

As discussed before, suitable stress promoter can also be a synthetic promoter, constructed by introduction of one or several HSE sequences, either isolated or amplified from natural stress genes, or synthesized chemically, into a non-stress-regulated promoter by recombinant techniques. A suitable stress promoter also includes a promoter containing variant HSE sequences. Single substitutions in the modules constituting an HSE are frequently tolerated. HSE are well conserved throughout the animal and plant kingdoms. A stress promoter therefore does not need to originate from a gene of the organism, in which or in cells of which a circuit will be established. For example, a fly stress promoter may be used in a functional circuit introduced in a mammalian cell. Amin et al., Mol. Cell. Biol. 5:197 (1985).

A gene of interest may be any gene encoding a useful RNA or protein. An encoded protein may be a secreted protein or a protein that is not secreted. The gene may or may not originate from the cell type in which a circuit is established. The gene may be of prokaryotic or eukaryotic origin, or may be prepared synthetically.

Examples of suitable genes for expression include genes for immunomodulators, such as cytokines, co-stimulatory molecules, stem cell growth factors, lymphotoxins, such as tumor necrosis factor, and hematopoietic factors, such as interleukins (e.g., interleukin-1 (IL-1), IL-2, IL-3, IL-4, IL-6, IL-10 and IL-12), colony stimulating factors (e.g., granulocyte-colony stimulating factor and granulocyte macrophage-colony stimulating factor), interferons (e.g., interferons-.alpha., -.beta. and -.gamma.), the stem cell growth factor designated "S1 factor," erythropoietin and thrombopoietin. Other suitable genes for expression include genes encoding toxins or protoxins, fusogenic proteins, stress proteins, foreign antigens, blood factors, polypeptide hormones, and other therapeutic proteins. More generally, the regulatory circuits described herein can be used to express any protein, in particular any protein in need of posttranslational modification, such as phosphorylation, glycosylation, methylation, acetylation, ubiquitination, and the like.

Vertebrate heat shock transcription factors (HSF) comprise several conserved sequence elements as well as a conserved functional element, which elements provide guidance for the design of mutated HSF. Conserved sequence elements include an amino-terminally located HSE DNA-binding domain having a helix-turn-helix binding motif defined by mutational and structural (X-ray crystallography and NMR) analyses, which motif is related to a motif in a bacterial sigma factor. Farther inside are two hydrophobic repeat regions of the 3,4-type, named HR1 and HR2. At least HR1 is essential for formation of the homotrimeric form of the factor, which is the form present in stressed cells and capable of binding HSE sequences. Farther inside, and separated from HR2 by more than 50 residues, is a third hydrophobic repeat, named HR3. HR2, HR3 and at least one portion of HR1 are important in the normal regulation of the oligomeric status of HSF. However, as is described below, this aspect of HSF regulation is of no consequence in the context of the invention. Sequences close to the carboxy terminus of the factor, beginning just amino-terminally from HR3, and possibly including HR3, contain transcriptional activation domains.

As was shown for both mammalian HSF1 and Drosophila HSF, over-expression of the factor from an exogenous gene results in accumulation of predominantly homotrimeric factor. Thus, over-expression overrides a first level of regulation of the factor, which is the conversion of monomer to homotrimer. Still, the over-expressed factor is transcriptionally inert. Hence, a second level of regulation that involves the conversion of inactive to active trimeric factor is still intact. Inactive, trimeric factor can be activated by stress or by manipulations that result in increased phosphorylation of the factor or a co-factor.

Over-expressed HSF can also be activated by mutation. Deletion or substitution in the region between about residues 185 and 315 in human HSF1 activates the factor as shown by its ability to transactivate a stress promoter-driven reporter gene in the absence of stress. This region includes HR2 and a stretch of about 115 residues immediately following the HR2 sequence. Specific example deletions are between residues 186 and 201, between 203 and 277, between 203 and 315 as well as various small deletions between residues 186 and 201. Activating substitutions can be made, for example, at residues 189, 191, 279, 298, 290-292 and 307. See, for example, Zuo et al., Mol. Cell. Biol. 14:7557 (1994), Zuo et al., Mol. Cell. Biol. 15:4319 (1995), Newton, et al., Mol. Cell. Biol. 16:839 (1996), and Xia et al., J. Biol. Chem. 273:8749 (1998). Based on sequence conservation, corresponding regions in other HSF can be readily identified.

DNA-binding domain sequences as well as HR sequences can be readily recognized in the sequence of an HSF. Mutations can be introduced into the HR2 region or in the region immediately following HR2. Many point mutations and virtually any sizeable deletion in these regions will activate the factor. Activating mutations can be identified, for example, by inserting a mutated HSF gene to be tested in an appropriate mammalian expression vector such as pcDNA3 (Invitrogen) containing a strong promoter such as a cytomegalovirus promoter. The resulting construct can be introduced in a reporter cell line such as HeLa-CAT (Baler et al., J. Cell Biol. 117:1151 (1992)), which contains a readily assayable reporter gene controlled by a stress promoter. In HeLa-CAT cells, the reporter gene is a chloramphenicol acetyltransferase gene and the stress promoter is that of the human hsp70B gene. The mutated HSF will be expressed in the transfected reporter cell, and, if the mutation is activating, will transactivate the reporter gene. Alternatively, any suitable cell line may be used, and the transactivation ability of the mutated HSF can be detected as an increase in the level of a stress protein, such as an Hsp70 or a small HSP.

Studies of mammalian HSF have also shown that the HSE DNA-binding domain can be replaced by another DNA-binding domain with the result that the substituted HSF can activate a gene controlled by a promoter containing recognition sites for the substituted DNA-binding domain but no longer interacts with stress genes. See, for example, Zuo et al., Mol. Cell. Biol. 14:7557 (1994), and Newton, et al., Mol. Cell. Biol. 16:839 (1996). The transcriptional activation domains of HSF can also be functionally substituted with other activation domains such as those active in other transcription factors. See, for example, Newton, et al., Mol. Cell. Biol. 16:839 (1996). Finally, HR3 is dispensable. Zuo et al., Mol. Cell. Biol. 15:4319 (1995); Newton, et al., Mol. Cell. Biol. 16:839 (1996).

Although human HSF, such as HSF1 and HSF2, and mutants thereof, are preferred heat shock transcription factors, other HSF (and their mutants) are suitable for use in a regulatory circuit described herein. In general, suitable HSF can be obtained from vertebrate sources, such as mammalian and avian sources, and from insect tissue. Examples of particular additional HSF include Drosophila melanogaster Dm-HSF, murine Mm-HSF1 and MmHSF2, and Gallus domesticus Gd-HSF1, Gd-HSF2, and Gd-HSF3. See, for example, Scharf et al., "Heat Stress Promoters and Transcription Factors," in Results and Problems in Cell Differentiation 20, Nover (Ed.), pages 125-162 (Springer-Verlag 1994), and Nover and Scharf, Cell. Mol. Life Sci. 53:80 (1997).

Thus, a mutated HSF useful in the invention contains a DNA-binding domain, either from an HSF or, in circuits discussed below, from another DNA-binding protein, a trimerization domain (HR1 sequences), and a transcription activation domain, either from an HSF or from another source. Depending on the size of mutated HSF, a nuclear localization signal should also be included in its sequence.

Nucleic acid molecules for constructing the various elements of a regulatory circuit as described herein can be obtained from sources where they naturally occur, from cloned DNA regions, by reverse transcription of RNA from cells in which they are expressed, or by chemical synthesis. The molecules can be joined by standard molecular biology techniques, making use of restriction enzyme sites, adapters, linkers or suitable PCR fragments.

3. Construction of a Type 2 Circuit

When the type 1 circuit is used, activation of the circuit not only results in sustained expression of the gene of interest but also of endogenous stress genes. As a consequence, cells containing the circuit will also accumulate stress proteins to higher than normal levels, which may result in a tolerant state. In this state, a cell may no longer proliferate, and has a substantially enhanced resistance to proteotoxic insults. Although this "resting" state can be maintained for a considerable period, it is suspected that it cannot be sustained indefinitely. Thus, resting cells may eventually die. In some applications, this may be a desired outcome. In other applications, however, one may wish to use circuits that will not place cells in a resting state.

Figure 2:
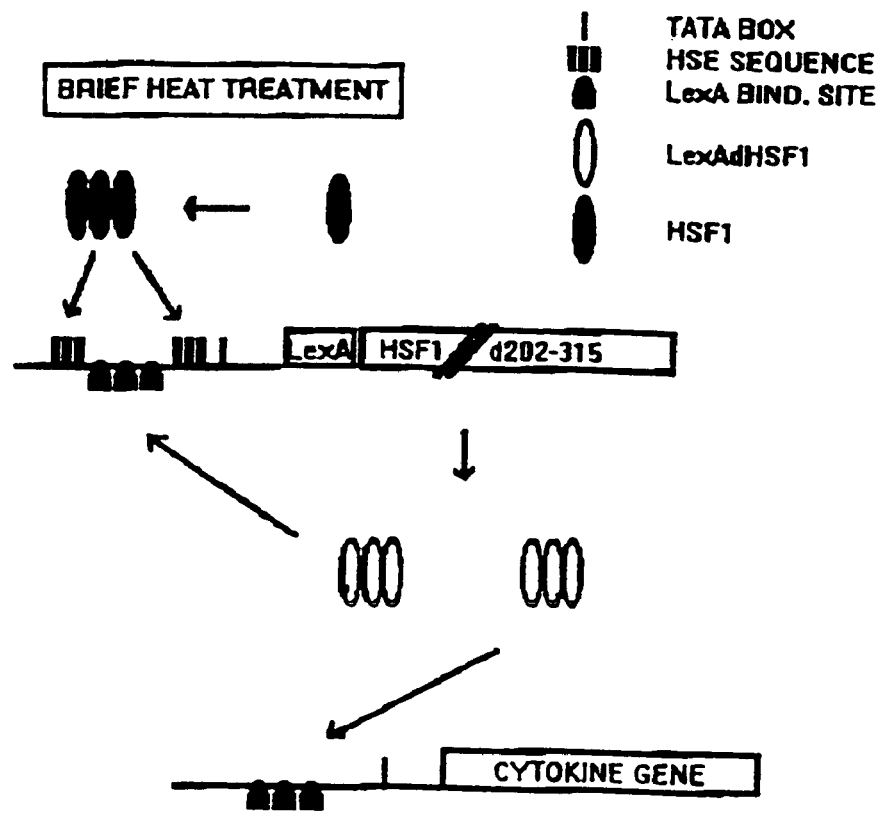
FIG. 2 is a schematic of the elements of a type 2 regulatory circuit and shows the interactions between the elements. "LexAdHSF" refers to a hybrid transcription factor gene encoding a constitutively active HSF1 with its heat shock element DNA-binding domain replaced by the DNA-binding domain of bacterial repressor LexA.

FIG. 2 shows an example of another type of stress-inducible circuit that will not stimulate continuous accumulation of stress proteins. The illustrative type 2 circuit shown in FIG. 2 differs from a type 1 circuit in three ways. First, the type 2 circuit contains a mutated HSF in which the HSE DNA-binding domain has been replaced by that of bacterial repressor LexA. This substituted factor no longer binds stress promoters but promoters containing LexA recognition sites. The properties of such a substituted factor have been documented in detail in the literature. See Zuo et al., Mol. Cell. Biol. 14:7557 (1994), and Zuo et al., Mol. Cell. Biol. 15:4319 (1995). Second, the promoter controlling the expression of the gene of interest contains LexA sites, so that it can be activated by a transcription factor recognizing these sites. See, for example, Zuo et al. Mol. Cell. Biol. 15:4319 (1995), for a description of such a promoter. Finally, the promoter controlling the expression of mutated HSF can be activated either by endogenous HSF or by mutated HSF, because it contains both functional HSE and LexA recognition sites. Such a promoter can be conveniently constructed, for example, by inserting in a stress promoter one or more copies of the known LexA motif. LexA motifs may be prepared chemically or may be retrieved from an existing promoter containing such motifs. See, for example, U.S. Pat. No. 4,833,080, and Garriga et al., Mol. Gen. Genet. 236:125 (1992). DNA molecules encoding the LexA repressor may be obtained from plasmid pRB500, American Type Culture Collection accession No. 67758.

A type 2 circuit operates as follows. After transient stress, endogenous HSF is activated, which results in expression and accumulation of mutated HSF. During and subsequent to stress, mutated HSF activates the promoter controlling the gene of interest as well as its own promoter, resulting in expression of the protein of interest as well as additional mutated HSF. The continued expression of mutated HSF stimulates synthesis of the protein of interest for an extended period or, possibly, until the cell's capacity is exhausted.

Normally, stress genes are only expressed during the initial transient stress. Subsequent to this triggering stress, HSF is returned to its inactive form, stress gene expression ceases, and stress proteins are eliminated by the cell's proteolytic machinery. Expression of mutated HSF may further accelerate deactivation of HSF: as mutated HSF is expressed at levels greatly exceeding that of endogenous HSF, HSF may be forced into heterotrimers consisting of two molecules of mutated HSF and one molecule of HSF. Since a single HSE DNA-binding domain is incapable of specifically binding the HSE sequence, the heterotrimers will be incapable of binding to and activating stress genes. The operation of the circuit can be assessed by experiments analogous to those described before for the more simple circuit. Similar types of precautions and manipulations as described before for the simpler circuit will ensure that the circuit is tightly stress-regulated.

A LexA DNA-binding domain in a mutated HSF can be substituted by the DNA-binding domain of many other DNA-binding proteins as long as it is added to an HSF sequence at a point amino-terminal from the HR1. This follows from structural studies showing that the region between the HSE DNA-binding domain and the HR1 is unstructured and therefore can accommodate another DNA-binding domain. Further support comes from observations that the LexA DNA-binding domain can be added at various positions amino-terminally from HR1, and the resulting chimeras have similar DNA-binding properties. Thus, the positioning of a DNA-binding domain relative to HSF sequences is not constrained, and therefore, construction of functional chimeras can be accomplished without additional experimentation. For each modified type 2 circuit, the gene of interest needs to be controlled by a promoter containing binding sites for the particular DNA-binding domain present in mutated HSF.

The type 2 circuit contains a gene encoding a mutated HSF comprising a DNA-binding domain other than an HSE DNA-binding domain that is constitutively active when expressed. The transcription factor gene is controlled by a promoter that can be activated by the mutated HSF and by endogenous HSF. This type of construct can be substituted by two constructs, the first comprising a transcription factor gene controlled by a stress promoter, and the second comprising a gene for the same transcription factor, or for a transcription factor binding the same nucleotide sequence as the first transcription factor, controlled by a promoter activatable by the transcription factor. The type 2 circuit also contains a gene of interest controlled by a promoter that can be activated by the transcription factor of the first element (second construct).

4. Construction of a Type 3 Circuit

Figure 3:
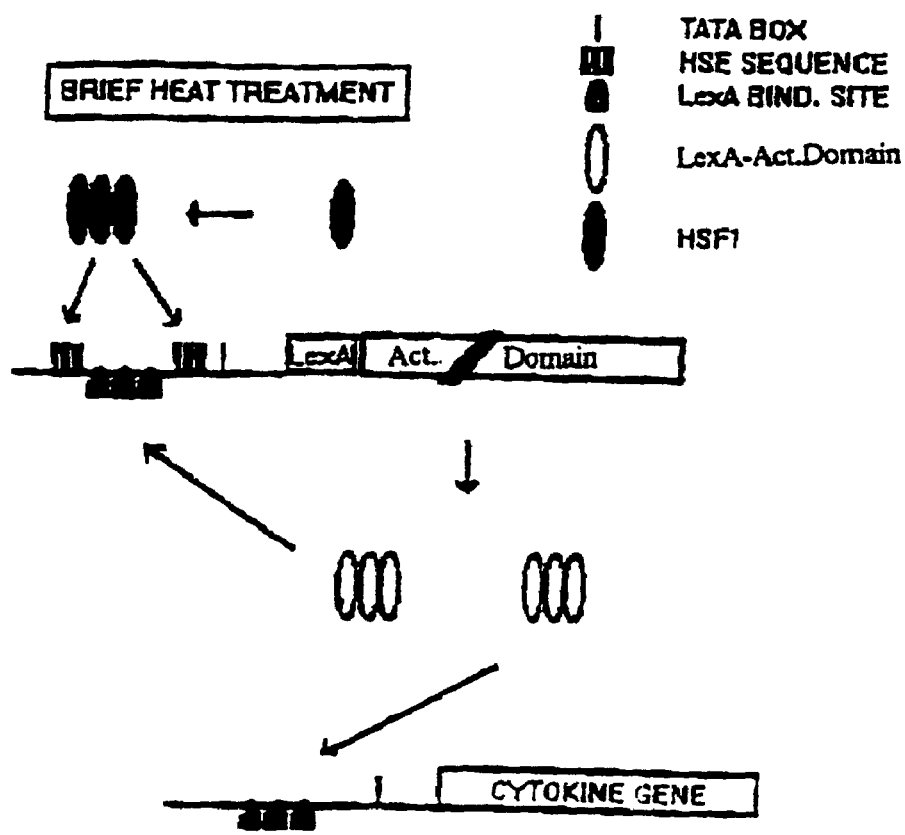
FIG. 3 is a schematic of the elements of one example of a type 3 regulatory circuit. "LexA-Act. Domain" refers to a hybrid transcription factor gene encoding the DNA binding and dimerization domains of LexA fused to a transcriptional activation domain.

Other forms of circuits can be constructed in which the transcription factor is not mutated HSF. That is, any constitutively active transcription factor can be used in lieu of mutated HSF. A type 3 circuit is illustrated in FIG. 3. Its elements are first a construct containing a gene for a constitutively active transcription factor, here the synthetic factor LexA-activation domain, linked to a promoter activatable by both a stress and the transcription factor. Transcription factor LexA-activation domain contains the DNA-binding and dimerization domains of bacterial repressor LexA fused to a transcriptional activation domain. Alternatively, two constructs, contained in one or two nucleic acids, can be substituted. One of the constructions contains the transcription factor gene linked to a stress promoter, and the other the transcription factor gene linked to a promoter responsive to the transcription factor. The second element is a construct containing a gene of interest controlled by a promoter responsive to the transcription factor.

Based on the same principles, more complex circuits can also be constructed, in which sustained expression of a gene of interest is regulated by stress and a second stimulus, which further decreases the likelihood of inadvertent activation. Such a system adds the new feature that expression of the gene of interest can be turned off at will.

Figure 4:
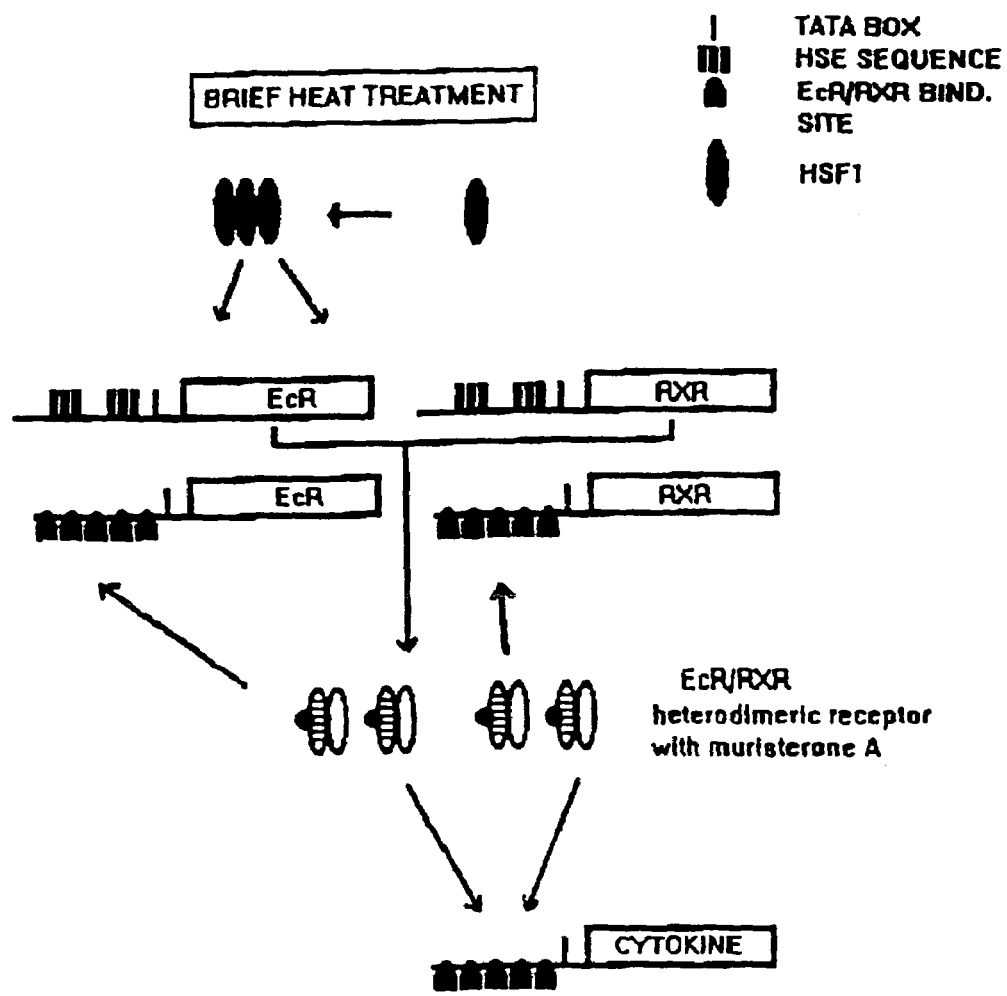
FIG. 4 is a schematic of the elements of another form of type 3 regulatory circuit. "EcR/RXR" refers to a heterodimeric ecdysone receptor composed of an ecdysone receptor (EcR) and a retinoid receptor (RXR) subunit.

An example of such a circuit that does not require mutated HSF and that, in addition, has the feature that a second stimulus is needed for activation of the gene of interest is illustrated in FIG. 4. In the example, the transcription factor is an artificial factor composed of two subunits, Drosophila ecdysone receptor (EcR) and retinoid receptor (RXR). The transcription factor is only active in the presence of an appropriate ligand, i.e., insect steroid hormone ecdysone or derivatives such as muristerone A. This ligand-activated transcription factor has been developed to permit regulation of expression of genes of interest in mammalian cells by insect-specific steroid hormone. Ecdysone-Inducible Expression Kit (Invitrogen Corp.; San Diego, Calif.).

The illustrated type 3 circuit contains two elements. First, there are two sets of constructs expressing the two subunits of EcR/RXR. One set is regulated by stress promoters, and the other by an artificial promoter activatable by EcR/RXR. Second, a gene of interest, such as a cytokine gene, is controlled by a promoter activatable by EcR/RXR. This form of type 3 circuit operates as follows. In the absence of either one or both, stress and hormone, the gene of interest is silent. In the presence of hormone, a transient stress will activate one set of transcription factor genes, resulting in accumulation of EcR/RXR that is activated by hormone. Active EcR/RXR will activate expression from the second set of transcription factor subunit genes as well as the gene of interest. Because the transcription factor is continually produced, activation of the gene of interest is sustained. Upon withdrawal of the hormone, transcription factor is inactivated, and the autoactivating loop is interrupted. The gene of interest is no longer expressed, and inactive transcription factor as well as protein of interest will eventually be degraded by intracellular proteolytic systems. This type of circuit may be particularly advantageous in the gene therapy setting, since it not only allows for local activation of a gene of interest by means of a local stress, but also for inactivation at the appropriate later time by means of withdrawal of systemically provided hormone.

As discussed before for type 2 circuits, the first element of the above type 3 circuit comprising two sets of constructs expressing the two subunits of transcription factor EcR/RXR may be substituted by single EcR and RXR genes, each of which genes is functionally linked to a dual-regulated promoter that is both responsive to activated (endogenous) HSF1 and to active EcR/RXR. Alternatively, making use of an internal ribosome entry site element, the two subunit genes may be controlled by a single promoter that is activatable by both a stress and active EcR/RXR. Such a promoter can be constructed, for example, by inserting in a stress promoter one or more copies of the known binding site for EcR/RXR. EcR/RXR motifs (E/GRE) may be prepared chemically or may be retrieved from an existing promoter containing such motifs. A minimal promoter containing multiple such motifs (E/GRE promoter) is present in construct pIND (www.invitrogen.com; Invitrogen Corporation). Experimentation revealed that insertion of EcR/RXR motifs PCR-amplified from pIND into the human hsp70B promoter resulted in a dual-regulated promoter. However, stress-induced activity was typically lower than that of the hsp70B promoter, and EcR/RXR-induced activity was lower than that of the pIND promoter. An alternative and generically useable strategy yielded dual-regulated promoters that were more highly active than the above promoters resulting from insertion of transcription factor binding sites into a stress promoter and that could be activated by stress and the transcription factor to levels comparable to those of the hsp70B promoter (activation by stress) and the pIND promoter (activation by EcR/RXR), respectively. The strategy consists of producing a combination promoter by inserting a transcription factor-responsive promoter into the associated RNA leader region of a stress gene promoter or a stress gene promoter into the associated RNA leader region of a transcription factor-responsive promoter. In a preferred embodiment of this approach, an intron sequence is introduced into the associated RNA leader region of a promoter activatable by the transcription factor, and a stress promoter is inserted into the intron sequence at a position that does not interfere with splicing. Alternatively, an intron sequence is introduced into the associated RNA leader region of a stress promoter, and a transcription factor-responsive promoter is inserted into the intron sequence at a position that does not interfere with splicing. The function of the intron sequence is to mediate the removal by splicing of sequences of the intron-inserted promoter from transcripts initiated in the upstream promoter.

The preparation and analysis of a combination promoter that is activatable by stress and by EcR/RXR is described in Example 3. Additional combination promoters were assembled according to the above strategy. For example, a combination promoter activatable by stress and transcription factors containing a DNA binding domain from yeast transcription factor GAL4 was constructed by insertion of a short intron sequence into the RNA leader region of the human hsp70B promoter. As described in detail in Example 4, a synthetic GAL4-responsive promoter was obtained from construct pGene/V5-His (www.invitrogen.com; Invitrogen Corp.) and introduced into the latter intron sequence by standard subcloning procedures. The resulting Hsp70/GAL4 combination promoter was linked to a firefly luciferase reporter gene and tested for stress inducibility and transcription factor inducibility in a cell line stably expressing chimeric transcription factor GLP65 (GeneSwitch™-3T3 cells from Invitrogen Corp.). Transcription factor GLP65 contains a GAL4 DNA-binding domain, a ligand-binding domain derived from a progesterone receptor and a transcription activation domain from NFkB p65. Burcin et al., Proc. Natl. Acad. Sci. USA 96:355 (1999). GLP65 is activated by the hormone mifepristone (formerly known as RU486).

Figure 6:
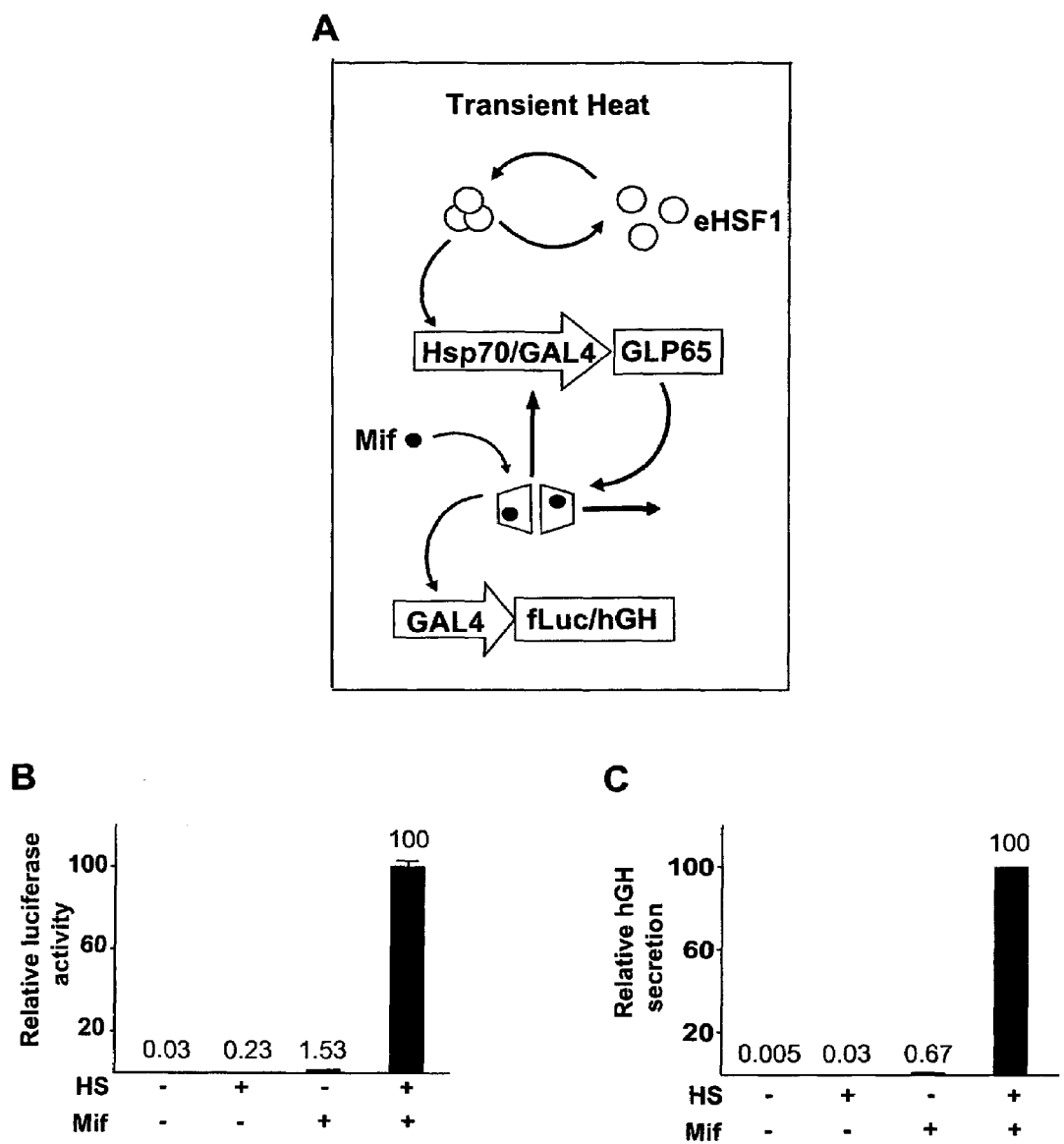
FIG. 6 shows in panel A a schematic of a type 3 regulatory circuit that incorporates a combination promoter. The regulated gene here is either a firefly luciferase gene (fLuc) or a human growth hormone gene (hGH). The transcription factor of this gene switch is GLP65, a mifepristone-activated chimeric factor that binds to and activates GAL4 binding site-containing promoters. Panels B and C provide results from luciferase assays or growth hormone assays, respectively, on cells containing the regulatory circuit that were either left untreated or were exposed to mifepristone (Mif) and/or stress (HS; heat treatment).

The above-described combination promoters can be used in molecular circuits comprising a first nucleic acid comprising a gene encoding a transcription factor operably linked to a combination promoter activatable by stress and the transcription factor and a second nucleic acid comprising a gene of interest operably linked to a promoter activatable by the transcription factor or to the combination promoter. The transcription factor may be a constitutively active transcription factor or a ligand-activated transcription factor. First and second nucleic acid molecules may be introduced into cells separately. Alternatively, they may be combined in a single nucleic acid molecule prior to introduction into cells. Example 5 describes results obtained with molecular circuits of this type. In the example circuits, a first nucleic acid comprises a gene for mifepristone-activatable transcription factor GLP65 that is operably linked to a combination promoter that is activatable by stress and GLP65 (the above-mentioned Hsp70/GAL4 promoter), and a second nucleic acid comprises a firefly luciferase gene (fLuc) or a human growth hormone gene (hGH) under the control of a promoter that responds to GLP65 (GAL4 promoter). See the schematic in FIG. 6 A. Results showed that the fLuc and hGH genes were essentially silent, except when the cells containing the respective gene switches were stressed (heat treatment) as well as were administered mifepristone (FIG. 6 B and C).

A nucleic acid comprising a gene encoding a transcription factor operably linked to a promoter activatable by stress and the transcription factor can also be used as a first element of a molecular circuit that incorporates a host cell gene including its own (operably linked) promoter. The promoter activatable by stress and the transcription factor may be a combination promoter or may be assembled by routine methods such as, for example, by insertion of transcription factor binding sites in a stress promoter. To provide an example of such a circuit that is constituted in the cell and uses a cellular gene as its second element, a nucleic acid encoding a p53 tumor suppressor gene operably linked to a promoter that is activatable by stress and p53 may be introduced into tumor cells lacking p53 or expressing a mutationally inactivated form of p53. The gene switch constituted in the cells comprises the transduced nucleic acid (first element) and the normal cellular target genes of p53 (second element) such as those for p21 (inhibits CDK), Bax (mediates apoptosis) or type I IGF receptor (inhibits tumor growth). Heat activation of the gene switch is expected to stop abnormal proliferation of the tumor cells. This type of gene switch may be useful in experimental gene therapy of p53-deficient tumors. Subsequent to delivery of the first nucleic acid to tumor cells as well as, unavoidably, also to non-tumor cells, the gene switch may be activated specifically in tumor cells by targeted heat, preventing undesired side effects or toxicity of p53 over-expression in non-tumor cells. Example 6 provides a proof-of-principle experiment demonstrating that a gene encoding a transcription factor operably linked to a promoter activatable by stress and the transcription factor and a target gene present in a host cell genome can constitute a functional regulatory circuit. In this experiment a stable cell line was created that contained in its genome a GAL4-promoter-controlled luciferase gene and a gene for transcription factor GLP65 operably linked to the Hsp70/GAL4 combination promoter. Luciferase expression in this cell line was found to be strictly dependent on stress (heat) activation and on the continuous presence of mifepristone.

The molecular circuits provided herein may be amplified by the inclusion of additional elements. For example, the gene of interest may be substituted with the gene for a transactivator, such as the TAT protein of HIV. As an additional element, a construct encoding the gene of interest functionally linked to a promoter activated by the transactivator or a host cell gene normally activatable by the transactivator, would be included in the molecular circuit. Once activated, this modified circuit may produce protein of interest at a higher rate than the original circuit. The different elements of such amplified circuits may be introduced into cells separately. Alternatively, two or more elements may be combined prior to introduction into cells.

5. Use of a Stress-Inducible Circuit to Prepare Recombinant Protein

The stress-inducible molecular circuits described above can be applied to mass production of proteins of interest. For example, a first construct can contain a gene of interest linked to a stress promoter. A second construct can include a stress promoter-regulated mutated HSF gene. Alternatively, a gene of interest and a mutated HSF gene can be combined in a single vector. Suitable vectors include a plasmid, cosmid, or viral vector. The construct or constructs may contain additional genes, for example, a gene encoding a selectable marker to facilitate isolation of stable cell lines containing the construct(s). The construct(s) is introduced along with a selectable marker gene (such as aminoglycoside 3'-phosphotransferase, dihydrofolate reductase, hygromycin β-phospho-transferase) into the host cell of choice by any method capable of delivering nucleic acids. Cell lines are selected, using a protocol adapted to the particular selectable marker employed.

Examples of suitable mammalian host cells include African green monkey kidney cells (Vero; ATCC CRL 1587), human embryonic kidney cells (293-HEK; ATCC CRL 1573), baby hamster kidney cells (BHK-21; ATCC CRL 8544), canine kidney cells (MDCK; ATCC CCL 34), Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCC CRL 1548), SV40-transformed monkey kidney cells (COS-1; ATCC CRL 1650) and murine embryonic cells (NIH-3T3; ATCC CRL 1658).

In addition, suitable insect host cells include cell lines derived from IPLB-Sf-21, a Spodoptera frugiperda pupal ovarian cell line, such as Sf9 (ATCC CRL 1711), Sf21AE, and Sf21 (Invitrogen Corporation; San Diego, Calif.), as well as Drosophila Schneider-2 cells. Established techniques for producing recombinant proteins in baculovirus systems are provided by Bailey et al., "Manipulation of Baculovirus Vectors," in Methods in Molecular Biology, Volume 7: Gene Transfer and Expression Protocols, Murray (ed.), pages 147-168 (The Humana Press, Inc. 1991), by Patel et al., "The baculovirus expression system," in DNA Cloning 2: Expression Systems, 2nd Edition, Glover et al. (eds.), pages 205-244 (Oxford University Press 1995), by Ausubel (1995) at pages 16-37 to 16-57, by Richardson (ed.), Baculovirus Expression Protocols (The Humana Press, Inc. 1995), and by Lucknow, "Insect Cell Expression Technology," in Protein Engineering: Principles and Practice, Cleland et al. (eds.), pages 183-218 (John Wiley & Sons, Inc. 1996).

Alternatively, the regulatory circuits described herein can be used to express a foreign protein in cultured yeast cells. Many yeast cloning vectors have been designed and are readily available. These vectors include YIp-based vectors, such as YIp5, YRp vectors, such as YRp17, YEp vectors such as YEp13 and YCp vectors, such as YCp19. One skilled in the art will appreciate that there are a wide variety of suitable vectors for expression in yeast cells.

Cell lines are tested for low level of expression of the gene of interest in the absence of stress and sustained expression following brief exposure of the cells to a stress by a protocol analogous to that described for the test circuit. For mass production of protein of interest, cells are grown in large scale on solid support or in reactors depending on the cell type. When an appropriate cell number is reached, production of the protein of interest is initiated by brief stress treatment. The stress treatment may be a heat shock treatment as described for the test system, or it may be a transient exposure to any of the chemicals and conditions that are known to activate stress promoters. Alternatively, cells may be exposed to a mild stress, which may be maintained throughout the protein production period. Whereas cells normally down-regulate expression from stress promoters after an initial burst of expression under such conditions, cells containing the regulatory circuit will not be able to do so, and expression will continue until the cells are exhausted.

Methods of inducing expression of genes controlled by a stress promoter are well known to those of skill in the art. In addition to heat, stress promoters can be activated, for example, by heavy metals, alcohols, benzoquinone ansamycins, sulfhydryl-reactive reagents, and oxidants. See, for example, Hegde et al., J. Cell. Physiol. 165:186 (1995), Wu, "Heat Shock Transcription Factors: Structure and Regulation," in Annu. Rev. Cell Dev. Biol. 11:441 (Annual Reviews, Inc. 1995), and Benndorf and Bielka, "Cellular Stress Response: Stress Proteins-Physiology and Implications for Cancer," in Recent Results in Cancer Research 143:130 (Springer-Verlag 1997).

At the appropriate time, cells are harvested and proteins of interest isolated or, if protein of interest is secreted, medium is collected and protein purified from medium using routine protocols. In the case of secreted proteins of interest, medium containing the proteins may be collected periodically or continuously. General methods for expressing and recovering foreign protein produced by a mammalian cell system is provided by, for example, Etcheverry, "Expression of Engineered Proteins in Mammalian Cell Culture," in Protein Engineering: Principles and Practice, Cleland et al. (eds.), pages 163 (Wiley-Liss, Inc. 1996). Established methods for isolating recombinant proteins from a baculovirus system are described by Richardson (ed.), Baculovirus Expression Protocols (The Humana Press, Inc. 1995).

6. Use of a Stress-Inducible Circuit for Gene Therapy

A regulatory circuit described herein can also be used to improve gene therapy methods. Gene therapy involves delivery of nucleic acids to cells of an individual, which may be expressed into therapeutic or prophylactically acting proteins in the target cells. In almost every conceivable situation, delivery cannot be targeted accurately to the area where therapy is necessary. Consequently, additional cells, tissues and organs that do not need the therapeutic nucleic acid are also provided with the nucleic acid. Oftentimes, such lack of proper targeting will have unwanted side effects. For example, if IL-2 needs to be expressed in a particular tissue to stimulate an appropriate immune response, untargeted delivery of an IL-2 gene may result in systemic expression of the cytokine. It is well known that systemic introduction of IL-2 has severe toxic side effects. This problem can be avoided by delivery of the two-element regulatory circuit described before, which in this example case would contain the IL-2 gene as the gene of interest. A standard delivery method can be used, resulting in delivery to the intended tissue as well as to certain other tissues. In the absence of a stress, the IL-2 gene of the circuit will be inactive. Activation and sustained expression of the gene in the proper location can then be achieved by transiently stressing the specific tissue, in which expression is desired.

Gene therapy can be targeted to monogenic diseases and to cancer. In a monogenic disease, correction of the gene defect in only one tissue may be sufficient to improve or to normalize the subject's condition. Examples of monogenic disease include Gaucher's disease (glucocerebrosidase deficiency), mucopolysaccharidosis β-glucuronidase deficiency), hyperammonemia (ornithine transcarbamylase deficiency), familial hypercholesterolemia (LDL receptor deficiency), hemophilia A (blood clotting factor VIII deficiency), phenylketonuria (phenylalanine hydroxylase deficiency), emphysema ($\alpha_1$-antitrypsin deficiency), Duchenne muscular dystrophy (dystrophin deficiency), and sickle-cell disease β-globin deficiency).

There are various approaches to treating cancer via gene therapy. For example, suicide genes that confer drug sensitivity can be transferred to cancer cells. Such transduced cancer cells are selectively eliminated due to their hypersensitivity to the drug. Gene therapy can also be used to transfer therapeutic genes that down-regulate oncogenes. Alternatively, cancer-promoting genes can be attacked using anti-sense genes, or targeted ribozymes. In another approach, recombinant antibody genes can be introduced into a subject to produce antibodies that interfere with tumor cell functions. Genes can also be introduced into a subject that enhance the subject's anti-tumor immune response. Such genetic approaches to cancer therapy are described, for example, by Davis et al., Curr. Opin. Oncol. 8:499 (1996), Rosenfeld and Curiel, Curr. Opin. Oncol. 8:72 (1996), Schmidt-Wolf and Schmidt-Wolf, Ann. Hematol. 73:207 (1996), Zhang and Russell, Cancer Metasis. Rev. 15:385 (1996), Blaese, Scientific American, page 91 (June 1997), and Roth and Cristiano, J. Natl. Cancer Inst. 89:21 (1997).

In addition to monogenic diseases and cancer, gene therapy can be directed to infectious diseases, such as AIDS, arterial diseases, rheumatoid arthritis, and degenerative neurological disorders.

There are numerous approaches to introduce a molecular circuit-regulated therapeutic gene to a subject, including the use of recombinant host cells that express a therapeutic gene in an ex vivo approach, delivery of naked nucleic acid encoding a therapeutic gene, use of a cationic lipid carrier with a therapeutic gene, and the use of viruses that express the therapeutic gene, such as recombinant retroviruses, recombinant adeno-associated viruses, recombinant adenoviruses, and recombinant Herpes simplex viruses. See, for example, Rosenberg et al., Science 242:1575 (1988), Wolff et al., Science 247:1465 (1990), Breakfield and Deluca, The New Biologist 3:203 (1991), LaSalle et al., Science 259:988 (1993), and Mulligan, Science 260:926 (1993).

Suitable recombinant viral vectors, include for example, adenoviral vectors (e.g., Kass-Eisler et al., Proc. Nat'l Acad. Sci. USA 90:11498 (1993); Kolls et al., Proc. Nat'l Acad. Sci. USA 91:215 (1994); Li et al., Hum. Gene Ther. 4:403 (1993); Vincent et al., Nat. Genet. 5:130 (1993); and Zabner et al., Cell 75:207 (1993); WO 94/26914, WO 93/9191), adenovirus-associated viral vectors (Flotte et al., Proc. Nat'l Acad. Sci. USA 90:10613 (1993); Ferrari et al., Nature Medicine 11:1295 (1997)), alphaviruses such as Semliki Forest Virus and Sindbis Virus (Hertz and Huang, J. Vir. 66:857 (1992); Raju and Huang, J. Vir. 65:2501 (1991); Xiong et al., Science 243:1188 (1989); U.S. Pat. No. 5,091,309; WO 92/10578; WO 95/07994); herpes viral vectors (e.g., U.S. Pat. Nos. 4,769,331, 4,859,587, 5,288,641 and 5,328,688; and international publication Nos. WO 94/14971 and WO 95/04139), parvovirus vectors (Koering et al., Hum. Gene Therap. 5:457 (1994), pox virus vectors (Ozaki et al., Biochem. Biophys. Res. Comm. 193:653 (1993); Panicali and Paoletti, Proc. Nat'l Acad. Sci. USA 79:4927 (1982)), pox viruses, such as canary pox virus or vaccinia virus (Fisher-Hoch et al., Proc. Nat'l Acad. Sci. USA 86:317 (1989); Flexner et al., Ann. N.Y. Acad. Sci. 569:86 (1989); U.S. Pat. Nos. 4,603,112, 4,769,330 and 5,017,487; WO 89/01973), and retroviruses (e.g., Baba et al, J. Neurosurg 79:729 (1993); Ram et al., Cancer Res. 53:83 (1993); Takamiya et al., J. Neurosci. Res. 33:493 (1992); Vile and Hart, Cancer Res. 53:962 (1993); Vile and Hart, Cancer Res. 53:3860 (1993); U.S. Pat. No. 5,219,740; EP 415,731; WO 90/07936; WO 91/0285, WO 94/03622; WO 93/25698; WO 93/25234; WO 93/11230; WO 93/10218). Within various embodiments, either the viral vector itself, or a viral particle which contains the viral vector may be utilized in the methods and compositions described below.

Adenoviruses can be made replication-deficient, can infect quiescent or terminally differentiated cells, and can be purified to high titers. See, for example, Kozarsky and Wilson, Curr. Opin. Genet. Dev. 3:499 (1993). In addition, adenovirus DNA does not integrate into the host genome, thus decreasing the risk of adenovirus-associated disease.

Herpes simplex virus-based vectors have the ability to deliver therapeutic genes to non-dividing cells, and the ability to infect many cell types in humans. See, for example, Fields (ed.), Virology, pages 527-561 (Raven Press 1985), and Pepose and Lieb, Invest. Ophthalmol. Vis. Sci. 35:2662 (1994). Those of skill in the art are capable of constructing recombinant HSV viruses, using standard techniques. HSV-1 DNA can be obtained, for example, from commercial sources such as the American Type Culture Collection (ATCC No. VR-260). Martuza et al., U.S. Pat. No. 5,585,096 (1996), for example, have described the production of replication-competent HSV to express a therapeutic gene in a subject. Due to a double mutation, these HSV vectors produce neither ribonucleotide reductase nor the product of the K34.5 gene.

High titer stocks of recombinant viruses capable of expressing therapeutic and transcription factor genes of a regulatory circuit can be obtained from infected mammalian cells using standard methods. For example, recombinant HSV can be prepared in Vero cells, as described by Brandt et al., J. Gen. Virol. 72:2043 (1991), Herold et al., J. Gen. Virol. 75:1211 (1994), Visalli and Brandt, Virology 185:419 (1991), Grau et al., Invest. Ophthalmol. Vis. Sci. 30:2474 (1989), Brandt et al., J. Virol. Meth. 36:209 (1992), and by Brown and MacLean (eds.), HSV Virus Protocols (Humana Press 1997).

Depending upon the particular use of gene therapy, it may be desirable to suppress the expression of an abnormal protein. This can be achieved by blocking the transcription or translation of the mutated gene product. For example, anti-sense molecules have been used to block the expression of gene products.

Alternatively, a stress-inducible expression vector can be constructed in which a regulatory element is operably linked to a nucleotide sequence that encodes a ribozyme. Ribozymes can be designed to express endonuclease activity that is directed to a certain target sequence in a mRNA molecule. See, for example, Draper and Macejak, U.S. Pat. No. 5,496,698; McSwiggen, U.S. Pat. No. 5,525,468; Chowrira and McSwiggen, U.S. Pat. No. 5,631,359; Robertson and Goldberg, U.S. Pat. No. 5,225,337.

In another approach, expression vectors can be constructed in which a regulatory element directs the production of RNA transcripts capable of promoting RNase P-mediated cleavage of mRNA molecules that encode the target protein. According to this approach, an external guide sequence can be constructed for directing the endogenous ribozyme, RNase P, to a particular species of intracellular mRNA, which is subsequently cleaved by the cellular ribozyme. See, for example, Altman et al., U.S. Pat. No. 5,168,053; Yuan et al., Science 263:1269 (1994); Pace et al., international publication No. WO 96/18733; George et al., international publication No. WO 96/21731; Werner et al., international publication No. WO 97/33991. Preferably, the external guide sequence comprises a ten to fifteen nucleotide sequence complementary to mRNA encoding a target protein of interest, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a regulatory circuit, such as a recombinant virus, will vary depending upon such factors as the subject's age, weight, height, sex, general medical condition and previous medical history. The dosage will also depend upon the particular gene of interest and the disease or condition that is targeted for treatment.

Suitable routes of administration of therapeutic vectors include intravenous injection, intraarterial injection, intraperitoneal injection, intramuscular injection, intratumoral injection, subcutaneous injection, and injection into a cavity that contains a tumor. Administration can be performed by continuous infusion or by single or multiple boluses.

A composition comprising therapeutic vectors of the present invention can be formulated according to known methods to prepare pharmaceutically useful compositions, whereby vectors or viruses are combined in a mixture with a pharmaceutically acceptable carrier. A composition is said to be a "pharmaceutically acceptable carrier" if its administration can be tolerated by a recipient subject. Sterile phosphate-buffered saline is one example of a pharmaceutically acceptable carrier. Other suitable carriers are well-known to those in the art. See, for example, Remington's Pharmaceutical Sciences, 19th Ed. (Mack Publishing Co. 1995), and Gilman's The Pharmacological Basis of Therapeutics, 7th Ed. (MacMillan Publishing Co. 1985).

For purposes of therapy, a therapeutic vector, or a recombinant virus comprising such a vector, and a pharmaceutically acceptable carrier are administered to a subject in a therapeutically effective amount. A combination of a therapeutic vector (or virus) and a pharmaceutically acceptable carrier is said to be administered in a "therapeutically effective amount" if the amount administered is physiologically significant. An agent is physiologically significant if its presence results in a detectable change in the physiology of a recipient subject.

After administration, vectors comprising regulatory circuits described herein must be activated in the subject. A preferred method of activating such a circuit is to apply heat to the location that would benefit from expression of the therapeutic gene. Selective localized heating of the inducible genes in target tissue with the body can be achieved using either non-invasive or invasive procedures. Non-invasive heating can be accomplished with focused ultrasound which has been shown to locally heat tissues in situations where the acoustic path from the surface of the body to the target tissue has no interceding air and bone. See, for example, Lele, J. Physiol. 160:494 (1962). Transducers for delivering the ultrasound are designed with specific dimensions and shapes for high intensity ultrasound focusing for different anatomical regions of the body. These ultrasound transducers can be constructed in an array so that acoustic power can be phased and the heat targeting can be highly controlled and localized.

Heat can also be delivered non-invasively to localized areas of the body using an adaptive phased radiowave array. Microwave power at, for example, 915 MHz, can be delivered with adaptive feedback focusing to control the energy delivered and, thus, the temperature in a localized area. Fenn, U.S. Pat. No. 5,251,645 (1993).

Localized heating within the body can also be performed by invasive procedures such as by introducing catheters and using imaging methods, such as 3D ultrasound or computerized tomography, to guide localization of a heating applicator in the target tissue. These applications can take the form of metal needles where heat is produced by connecting the ends of the needles that are outside the body to a source of radio-frequency power. Alternatively, the catheters could serve as guides for optical fibers to deliver laser energy to produce localized heating.

Local stress may also be applied by application of a chemical activator of stress promoters such as, for example, a heavy metal or a benzoquinone ansamycin compound. Local application may be achieved by direct injection into the target tissue. For many chemicals, the concentration needed to activate a stress promoter in cells of a particular organism is well known. Persons skilled in the art will know how to achieve the required concentration in a particular tissue or how to obtain the relevant information.

Unlike in the protein production setting where activation at a low stress threshold may be acceptable or even desired, in the gene therapy setting it is important that a regulatory circuit is only triggered at highest possible level of stress. Stress promoters are only strongly active at temperatures of 41-42° C. and above in human cells. Such temperatures, corresponding to extreme fever, are only reached rarely in humans. In fact, a prudent physician will do everything possible to prevent a patient from developing such fever to avoid consequences such as seizures. Thus, except under the most unusual circumstances, stress promoters will not be activated inadvertently in humans. Regulatory circuits can be built to have a similarly high threshold level of activation by carefully choosing a strictly stress-regulated promoter and, if necessary, introducing other modifications as discussed before to reduce the level of accumulation of mutated HSF. Inadvertent activation can also be avoided by the use of a regulatory circuit comprising a gene for a ligand-activated transcription factor.

The present invention, thus generally described, will be understood more readily by reference to the following examples, which are provided by way of illustration and are not intended to be limiting of the present invention.

EXAMPLE 1

Construction and Operation of a Test Circuit

The exemplary test circuit contains two elements. The first element consists of a plasmid containing a stress promoter-regulated firefly luciferase gene. To prepare this construct, 10 µg of plasmid 173OR, described by Voellmy et al., Proc. Natl. Acad Sci. USA 89:4949 (1985), are digested with 25 units of restriction enzymes XhoI and HindIII for two hours at 37° C., using a digestion buffer suggested by the supplier (New England Biolabs, Inc., Beverly, Mass.). The digest is electrophoresed on a 0.9% agarose gel, and DNA fragments are visualized by ethidium bromide staining. A 2.7 kbp fragment is excised, electroeluted, purified by phenol-chloroform-isoamyl alcohol and chloroform extraction and ethanol precipitation, and resuspended in a small volume of water. The 2.7 kbp fragment contains the promoter and a portion corresponding to essentially the entire RNA leader sequence of the human hsp70B gene. A 5 µg aliquot of pGL3-Basic Vector (Promega, Madison, Wis.), containing a promoter-less firefly luciferase gene, is similarly double-digested with XhoI and HindIII, purified by phenol-chloroform-isoamyl alcohol and chloroform extraction and ethanol precipitation, and resuspended in a small volume of water. Standard ligation reaction is carried out containing about 1 µg of p1730R fragment and 0.25 µg of digested pGL3-Basic Vector. The ligation reaction is used to transform MC1061 $E.$ $coli$ host cells. Ampicillin-resistant transformants are recovered, and plasmid DNA is prepared from transformant cultures by a standard procedure. The identity of the intended construct, hsp70B-luciferase, in which the hsp70B promoter segment is inserted in the correct orientation immediately upstream from the luciferase-coding sequence is determined by extensive restriction analysis.

To functionally test the construct, HeLa cells are transfected by the Lipofectamine.TM. method (Gibco-BRL) with 2-10 µg of hsp70B-luciferase DNA per 60 mm dish containing 70%-confluent HeLa cells. One day after transfection, one of two parallel cultures is heat-treated at 42-44° C. for 1 hour in a waterbath, and the parallel cultures are incubated for several hours at 37° C. Cells are harvested, extracts prepared and luciferase activity measured by a standard procedure. Readily measurable luciferase activity can be seen in extracts from heat-treated, transfected cultures, but not from transfected cultures that have not been heat-treated, or from untransfected cultures.

The second element consists of a plasmid containing an HSF1 mutant gene, HSF1d202-316, which is described in Zuo et al., Mol. Cell. Biol. 15:4319 (1995), and a functionally linked hsp70B promoter. To construct this plasmid, p173OR DNA is digested with BamHI and EcoRI as described above, and a 2 kbp BamHI-EcoRI fragment containing 3' nontranslated sequences from a Drosophila hsp70 gene is isolated. Another aliquot of p173OR DNA is digested with EcoRI and HindIII, and a fragment about 5 kbp in length containing plasmid sequences including an ampicillin resistance gene and hsp70B promoter and RNA leader sequences is isolated. Finally, a HindIII-BglII fragment about 1.8 kbp in length containing the HSF1d202-316-coding region is isolated from a pGem3Zf(+) plasmid clone carrying the mutated HSF1 sequence (Zuo, J. (1994) Ph.D. Thesis, University of Miami, Miami, Fla.). The three fragments are co-ligated and transformed, and transformants analyzed as described before. The correct plasmid identified in this way, named (p)(hsp70B-mutated HSF1, contains, in a plasmid sequence background derived from p1730R, hsp70B promoter and RNA leader sequences linked to the beginning of the mutated HSF1 gene and Drosophila 3' nontranslated sequences linked to the end of the mutated HSF1 gene.

To evaluate the test circuit consisting of a combination of the above two plasmids, parallel sets HeLa cell cultures are transfected with a plasmid expressing luciferase constitutively (for example, pRL-CMV Vector (Promega)) as a positive control, with hsp70B-luciferase or co-transfected with both hsp70B-luciferase and hsp70B-mutated HSF1. To optimize the system, co-transfections should be carried out at different ratios of the two plasmids. One day after transfection, one set of cultures is subjected to 42-44° C. /1 hour heat treatment, and all cultures are further incubated for two to three days at 37° C. Cells are then harvested, extracts prepared, and luciferase activity measured by a standard procedure.

To verify equal transfection of cultures, all transfection solutions may contain a gene encoding enhanced green fluorescent protein, and transfection efficiency is monitored by counting fluorescing cells under a fluorescence microscope. Alternatively, a portion of cells may be set aside at the time of harvest for cytometric determination of transfection efficiency. If the circuit is operating satisfactorily, co-transfected cells that have not been heat-treated should contain low luciferase activity, comparable to that of non-heat-treated cells transfected singly with hsp70B-luciferase. In contrast, heat-treated, co-transfected cells should show luciferase activity that is orders of magnitude greater than that measured in unheated, co-transfected cells and at least one order of magnitude greater than that present in heat-treated cells singly transfected with hsp70B-luciferase. Luciferase activity in heat-treated, co-transfected cells will be equal or greater than that in cells transfected with the construct constitutively expressing luciferase.

EXAMPLE 2

Construction of a Circuit for the Mass Production of Human Growth Hormone

An example circuit for the production of human growth hormone contains the following two elements: hsp70B-mutated HSF1 and a plasmid containing a cDNA gene encoding human growth hormone functionally linked to the hsp70B promoter. The latter plasmid can be plasmid 17hGHdhfr. Dreano et al., Gene 49:1 (1986).

The operation of the circuit is as follows. HeLa cells transfected with p17hGHdhfr do not produce growth hormone in the absence of stress. When cells are stressed by a 42° C./1 hour heat treatment, expression of growth hormone is induced and can be measured in the medium by a standard radioimmunoassay, as described, for example, by Dreano et al., Gene 49:1 (1986). Expression of growth hormone ceases about one day after heat treatment. In contrast, expression of growth hormone continues in cells co-transfected with p17hGHdhfr and phsp70B-mutated HSF1 for several days after heat treatment.

EXAMPLE 3

Preparation and Analysis of a Construct Comprising a Firefly Luciferase Gene Operably Linked to a Combination Promoter (Hsp70/E/GRE) Activatable by Stress and Active EcR/RXR E/GRE-fLuc was constructed by ligation of a HindIII-SalI fragment from GL3B (Promega Corp.) including firefly luciferase-coding sequences and HindIII/XhoI-digested pIND DNA. Reporter gene construct Hsp70-fLuc was obtained by subcloning promoter and RNA leader sequences of the human hsp70B gene from OR173 into a plasmid containing a firefly luciferase gene. To prepare Hsp70/E/GRE-fLuc, an SgfI site was inserted in the Hsp70B 5' untranslated region present in Hsp70-fLuc by the QuikChange procedure (Stratagene Corp.) using primer 5'-CAGCCTCCGTGGCCTCGCGATCGCAG-CATCCGACAAGAAGC-3' (SEQ ID NO: 4) and its complement. The resulting construct was named Hsp70/E/GRE-fLuc/Sgf. A short intron sequence (about 245 bp) was PCR-amplified from construct RL-CMV (Promega Corp.) using primers 5'-TATGCGATCGCTTCTGACACAA-CAGTCTCG-3' (SEQ ID NO: 5) and 5'-TATGCGATCGC-CTTAAGAGCTGTAATTGAAC-3' (SEQ ID NO: 6), digested with SgfI and ligated to SgfI-digested Hsp70/E/GRE-fLuc/Sgf. The resulting construct Hsp70/E/GRE-fLuc/Sgf/Int served as template in a QuikChange reaction designed to introduce an AscI restriction site into the intron sequence (construct Hsp70/E/GRE-fLuc/Sgf/Int/Asc). Primers employed were 5'-TATGGCGCGCCACCT-GACGTCGACGG-3' (SEQ ID NO: 7) and 5'-ATAG-GCGCGCCGGTAAGCTTAAGTTTAAACGCTAGC-3' (SEQ ID NO: 8). Finally, a fragment of about 500 bp in length containing a minimal E/GRE promoter was PCR-amplified from construct pIND (Invitrogen Corp.) using appropriate primers containing AscI sites at their 5' ends, digested with AscI and ligated to AscI-cut Hsp70/E/GRE-fLuc/Sgf/Int/Asc DNA to produce Hsp70/E/GRE-fLuc. All subcloning and mutagenesis steps were carried out using routine molecular biology technology and were monitored by restriction analysis and nucleotide sequencing.

To test the Hsp70/E/GRE combination promoter and compare it with the hsp70B and E/GRE promoters, EcR-293 cells were co-transfected using Lipofectamine™ reagent (Life Technologies) with Hsp70/E/GRE-fLuc, Hsp70-fLuc or E/GRE-fLuc and pRL-CMV containing a constitutively expressed Renilla luciferase gene. One day after transfection, parallel cultures were either left untreated or were subjected to a heat treatment at 43-44° C. for 30 min or to ponasterone A (Invitrogen Corp.) for 1-2 days. Cells were harvested (after ponasterone exposure or 6-7 h after heat treatment), and firefly luciferase activities were determined using the Dual Luciferase Reporter System (Promega Corp.). Results revealed that the Hsp70/E/GRE combination promoter was strongly inducible by heat and ponasterone A. Induced activities were comparable to those of the Hsp70 and E/GRE promoters. EcR-293 cells expressing activatable EcR/RXR were obtained from Invitrogen Corporation and were cultured according to the manufacturer's instructions.

EXAMPLE 4

Preparation and analysis of a construct comprising a firefly luciferase gene operably linked to a combination promoter (Hsp70/GAL4) activatable by stress and an active transcription containing a GAL4 DNA-binding domain.

To construct GAL4-fLuc, a HindIII (filled)-XhoI fragment from 17×4 TATA CAT (Wang et al., Nat. Biotechnol. 15:239 (1997); Wang et al., Gene Ther. 4:432 (1997)) including a GAL4-responsive promoter was inserted in between the SmaI and XhoI sites of GL2B. Reporter gene construct Hsp70-fLuc was obtained by subcloning promoter and RNA leader sequences of the human Hsp70B gene from OR173 into a plasmid containing a firefly luciferase gene. To prepare Hsp70/GAL4-fLuc, an SgfI site was inserted in the hsp70B 5' untranslated region present in Hsp70-Luc by the QuikChange procedure (Stratagene Corp.) using primer 5'-CAGCCTCCGTGGCCTCGCGATCGCAG-CATCCGACAAGAAGC-3' (SEQ ID NO: 9) and its complement. The resulting construct was named Hsp70/GAL4-fLuc/Sgf. A short intron sequence (about 245 bp) was PCR-amplified from construct RL-CMV (Promega Corp.) using primers 5'-TATGCGATCGCTTCTGACACAA-CAGTCTCG-3' (SEQ ID NO: 10) and 5'-TATGCGATCGC-CTTAAGAGCTGTAATTGAAC-3' (SEQ ID NO: 11), digested with SgfI and ligated to SgfI-digested Hsp70/GAL4-fLuc/Sgf. The resulting construct Hsp70/GAL4-fLuc/Sgf/Int served as template in a QuikChange reaction designed to introduce an AscI restriction site into the intron sequence (construct Hsp70/GAL4-fLuc/Sgf/Int/Asc). Primers employed were 5'-TATGGCGCGCCACCTGACGTC-GACGG-3' (SEQ ID NO: 12) and 5'-ATAGGCGCGCCG-GTAAGCTTAAGTTTAAACGCTAGC-3' (SEQ ID NO: 13). Finally, a fragment of about 450 bp in length containing a minimal GAL4 promoter was PCR-amplified from construct GeneV5-HisA (Invitrogen Corporation) using primers 5'-TATGGCGCGCCTCGACGGATCGGGAGATC-3' (SEQ ID NO: 14) and 5'-TATGGCGCGCCTGTTAATTAA-CACGGGG-3' (SEQ ID NO: 15), digested with AscI and ligated to AscI-cut Hsp70/GAL4-fLuc/Sgf/Int/Asc DNA to produce Hsp70/GAL4-fLuc. All subcloning and mutagenesis steps were carried out using routine molecular biology technology and were monitored by restriction analysis and nucleotide sequencing.

To test the Hsp70/GAL4 combination promoter and compare it with the hsp70B and GAL4 promoters, GeneSwitch™-3T3 cells were co-transfected using Lipofectamine™ reagent (Life Technologies) with Hsp70GAL4-fLuc, Hsp70-fLuc or GAL4-fLuc and pRL-CMV containing a constitutively expressed Renilla luciferase gene. One day after transfection, parallel cultures were either left untreated or were subjected to a heat treatment at 43-44° C. for 30 min or to 1-10 nM mifepristone (Sigma Corp.) for 1-2 days. Cells were harvested (after mifepristone exposure or 6-7 h after heat treatment), and firefly luciferase activities were determined using the Dual Luciferase Reporter System (Promega Corp.). Results revealed that the Hsp70/GAL4 combination promoter was strongly inducible by heat and mifepristone. Induced activities were significantly greater than those of the hsp70B and GAL4 promoters. GeneSwitch™-3T3 cells expressing mifepristone-activatable transcription factor GLP65 were obtained from Invitrogen Corporation and were cultured according to the manufacturer's instructions.

EXAMPLE 5

For the construction of Hsp70/GAL4-GLP65, a QuikChange reaction using primer 5'-CGAGTCTA-GAGATATCGAATTCAGGCGCGCCTTGTC-GACTCGAAGATCTG-3' (SEQ ID NO: 16) and its complement was performed to insert an AscI site downstream of the multicloning site of pShuttle (Stratagene Corp.). The resulting construct was named A1. A GLP65 gene fragment was PCR-amplified from pSwitch (Invitrogen Corp.) using primers 5'-TATTCTAGAACCAAGCTACCGGTCCACC-3' (SEQ ID NO: 17) and 5'-ATAGGCGCGCCTCAGAAGC-CATAGAGCCC-3' (SEQ ID NO: 18). The PCR fragment was digested with AscI and XbaI and ligated to AscI/XbaI-cut A1 DNA to yield construct 1A. Finally, an Hsp70/GAL4 promoter cassette was PCR-amplified using Hsp70/GAL-fLuc as template and primers 5'-TATGCGGCCGCTGGAA-GAGAAGGTTGG-3' (SEQ ID NO: 19) and 5'-TATGCG-GCCGCACAAGCTTCTTGTCGGATG-3' (SEQ ID NO: 20). The PCR fragment was digested with NotI and inserted into NotI-cut construct 1A. Note that the single NotI site in construct 1A is located within the pShuttle polylinker sequence, i.e., immediately upstream from the GLP65 gene. 17×4 TATA-hGH (renamed GAL4-hGH herein for consistency) has the backbone of 17 TATA CAT CAT (Wang et al., *Nat. Biotechnol.* 15:239 (1997); Wang et al., *Gene Ther.* 4:432 (1997)) and includes a human growth hormone gene.

To test the molecular circuits outlined in FIG. 6A, human HeLa cells were co-transfected with appropriate amounts of Hsp70/GAL4-GLP65 and GAL4-fLuc or GAL4-hGH using Lipofectamine™ reagent (Life Technologies). For correction of differences in transfection efficiency, a small amount of pRL-CMV expressing a Renilla luciferase was also included in transfection mixtures. One day after transfection, cultures were either left untreated, were administered 10 nM mifepristone, were heat-treated (43-44° C. for 30-60 min), or were administered mifepristone and subjected to heat treatment. Two or three days later, cells were harvested and assayed for firefly luciferase activity using the Dual Luciferase Reporter Assay System (Promega Corp.) or for hGH activity using an ELISA kit distributed by Roche, respectively. In each experiment, relative firefly luciferase/hGH activities are presented as fractions of the highest activity. Results are shown in FIG. 6 B and C.

EXAMPLE 6

Hsp70/GAL4-GLP65-34C was obtained from a QuikChange mutagenesis reaction using oligonucleotide 5'-ACCAAGCTACCGGTCCTCCATGTACTC-CCAGCAGCCAGATCTGAAGC-3' (SEQ ID NO: 21) and its complement as primers and Hsp70/GAL4-GLP65 DNA as template. The reaction replaced nucleotides at positions −3 and +4 relative to the GLP65 initiation codon with nucleotides that are less favorable for initiation of translation. To change the orientation of transactivator genes relative to vector sequences, GLP65 and GLP65-34C genes were PCR-amplified from Hsp70/GAL4-GLP65 and Hsp70/GAL4-GLP65-34C, respectively, using forward primer 5'-ATACCTAGGCGGATCCGACCTCCCACAGC-3' (SEQ ID NO: 22) and reverse primer 5'-ATAGCGGCCGCT-TGTCTTCCCAATCCTCCCC-3' (SEQ ID NO: 23), and the amplified fragments were digested with AvrII and NotI and ligated to NotI/XbaI-digested vector pShuttle. The resulting constructs were named Hsp70/GAL4-GLP65-R and Hsp70/GAL4-GLP65-RK, respectively. The same subcloning strategy was used to simultaneously change transactivator gene orientation and delete 3'-nontranslated sequences of transactivator genes, except that the reverse primer was 5'-AT-AGCGGCCGCCCGGAGGATCCTTAGGAGC-3' (SEQ ID NO: 24). The resulting constructs were labeled Hsp70/GAL4-GLP65-RC and Hsp70/GAL4-GLP65-RKC, respectively.

Figure 7:
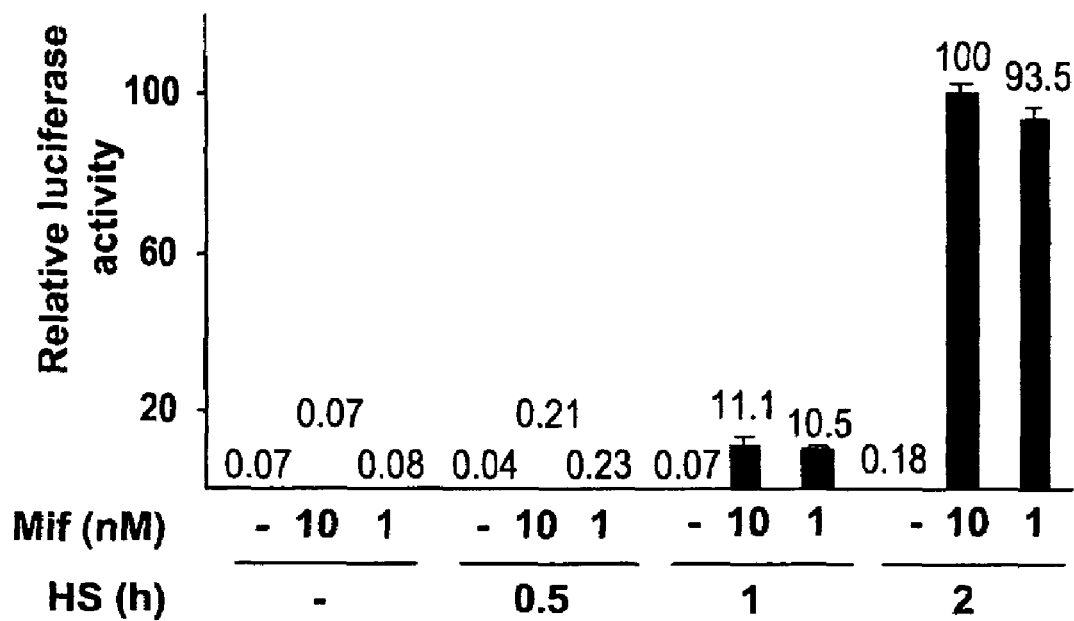
FIG. 7 provides results from luciferase assays on cells containing stably integrated in their genome a target luciferase gene and an Hsp70/GAL4-GLP65-RKC transactivator element. The cells were either left untreated or were exposed to mifepristone (Mif) and/or stress (HS; heat treatment).

To obtain cell lines containing in their genome an Hsp-based, mifepristone-dependent gene switch and a target luciferase gene, a promoter-less cDNA3.1 vector (expressing a neomycin resistance gene) was prepared by BamHI/BglII digestion of pcDNA3.1 followed by religation. The Hsp70/GAL4-GLP65-RKC gene was transferred to the latter vector to yield Hsp70/GAL4-GLP65-RKC-neo. HeLa-CAT cells were cotransfected with GAL4-fLuc and Hsp70/GAL4-GLP65-RKC-neo (4:1 molar ratio), and transformants were selected using 400 µg/ml G418. Clonal lines were isolated. Analysis of expression of the genomic luciferase gene in one such line demonstrated that it is properly regulated by the Hsp70/GAL4-GLP65-RKC transactivator element (FIG. 7). In the experiment shown in the Figure, parallel cultures of the cell line were either left untreated, or were heat-treated at 43° C. for the times indicated, exposed to mifepristone at the concentrations indicated, or both heat-treated and provided mifepristone. One day later, cells were harvested and assayed for firefly luciferase activity. Elevated levels of luciferase activity were only measured in cells that were both administered mifepristone and had been subjected to heat treatment, demonstrating that the genomic luciferase gene was correctly regulated by the transactivator element. Note that relative firefly luciferase activities are presented as fractions of the highest activity in the experiment.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

The invention claimed is:

1. A molecular circuit delivered into a cell, comprising (a) a first nucleic acid comprising a gene encoding a transcription factor, the gene being operably linked to a combination promoter activatable by stress and by the transcription factor, the combination promoter comprising a nucleotide sequence including a stress promoter and an associated RNA leader sequence into which a promoter activatable by the transcription factor is inserted or a nucleotide sequence including a promoter activatable by the transcription factor and an associated RNA leader into which a stress promoter is inserted, and (b) a second nucleic acid comprising a gene of interest, the gene of interest being operably linked to a promoter activatable by the transcription factor.

2. The molecular circuit of claim 1, wherein a single nucleic acid molecule comprises the first and second nucleic acids.

3. The molecular circuit of claim 1, wherein the promoter operably linked to the gene of interest is also a combination promoter activatable by stress and the transcription factor.

4. The molecular circuit of claim 3, wherein the gene encoding the transcription factor and the gene of interest are present on the same nucleic acid and are operably linked to a single combination promoter activatable by stress and the transcription factor.

5. The molecular circuit of claim 1, wherein the combination promoter comprises a nucleotide sequence including a stress promoter and an associated RNA leader sequence into which an intron sequence including a promoter activatable by the transcription factor is inserted or a nucleotide sequence including a promoter activatable by the transcription factor and an associated RNA leader into which an intron sequence including a stress promoter is inserted.

6. The molecular circuit of claim 5, wherein the combination promoter comprises a nucleotide sequence from the human Hsp70B stress gene including a stress promoter and an RNA leader sequence into which an intron sequence including a promoter activatable by the transcription factor is inserted.

7. The molecular circuit of claim 5, wherein the transcription factor is EcR/RXR or a transcription factor comprising a GAL4 DNA-binding domain and the combination promoter comprises a nucleotide sequence from the human Hsp70B stress gene including a stress promoter and an associated RNA leader sequence into which an intron sequence including a promoter activatable by the transcription factor is inserted.

8. A nucleic acid comprising a gene encoding a transcription factor, the gene being operably linked to a combination promoter activatable by stress and by the transcription factor, the combination promoter comprising a nucleotide sequence including a stress promoter and an associated RNA leader sequence into which a promoter activatable by the transcription factor is inserted or a nucleotide sequence including a promoter activatable by the transcription factor and an associated RNA leader into which a stress promoter is inserted.

9. A nucleic acid according to claim 8, wherein the combination promoter comprises a nucleotide sequence including a stress promoter and an associated RNA leader sequence into which an intron sequence including a promoter activatable by the transcription factor is inserted or a nucleotide sequence including a promoter activatable by the transcription factor and an associated RNA leader into which an intron sequence including a stress promoter is inserted.

10. A nucleic acid according to claim 9, wherein the combination promoter comprises a nucleotide sequence from the human Hsp70B stress gene including a stress promoter and an RNA leader sequence into which an intron sequence including a promoter activatable by the transcription factor is inserted.

11. A molecular circuit constituted in a host cell, comprising (a) a nucleic acid delivered into the cell comprising a gene encoding a transcription factor, the gene being operably linked to a promoter or combination promoter activatable by stress and by the transcription factor, and (b) a gene of the host cell that is activatable by the transcription factor.

12. A molecular circuit constituted in a host cell, comprising (a) a nucleic acid delivered into the cell comprising a gene encoding a first transcription factor, the gene being operably linked to a promoter or combination promoter activatable by stress and by the first transcription factor, (b) a nucleic acid delivered into the cell comprising a gene for a second transcription factor, the gene being operably linked to a promoter activatable by the first transcription factor, and (c) a gene of the host cell that is activatable by the second transcription factor.

13. The molecular circuit of claim 12, wherein the genes for first and second transcription factors are present on a single nucleic acid.

14. A molecular circuit constituted in a host cell, comprising (a) a nucleic acid delivered into the cell comprising a gene encoding a first transcription factor, the gene being operably linked to a stress promoter, (b) a nucleic acid delivered into the cell comprising a gene for a second transcription factor, the gene being operably linked to a promoter or combination promoter activatable by the first and second transcription factors, and (c) a gene of the host cell that is activatable by the second transcription factor.

15. The molecular circuit of claim 14, wherein both transcription factor genes are present on a single nucleic acid.

16. The molecular circuit of claim 14, wherein the first and second transcription factors are identical.

* * * * *

SEQUENCE LISTING

```
<160> NUMBER OF SEQ ID NOS: 3

<210> SEQ ID NO 1
<211> LENGTH: 2156
<212> TYPE: DNA
<213> ORGANISM: Artificial Sequence
<220> FEATURE:
<223> OTHER INFORMATION: Unknown
<220> FEATURE:
<221> NAME/KEY: CDS
<222> LOCATION: (161)...(1747)

<400> SEQUENCE: 1
cgggcccgtt gcaagatggc ggcggccatg ctgggccccg gggctgtgtg tgcgcagcgg      60
gcggcggcgc ggcccggaag gctggcgcgg cgacggcgtt agcccggccc tcggcccctc     120
tttgcggccg ctccctccgc ctattccctc cttgctcgag atg gat ctg ccc gtg     175
                                              Met Asp Leu Pro Val
                                                1               5
```

-continued

| | |
|---|---|
| ggc ccc ggc gcg gcg ggg ccc agc aac gtc ccg gcc ttc ctg acc aag<br>Gly Pro Gly Ala Ala Gly Pro Ser Asn Val Pro Ala Phe Leu Thr Lys<br>          10                15                20 | 223 |
| ctg tgg acc ctc gtg agc gac ccg gac acc gac gcg ctc atc tgc tgg<br>Leu Trp Thr Leu Val Ser Asp Pro Asp Thr Asp Ala Leu Ile Cys Trp<br>          25                30                35 | 271 |
| agc ccg agc ggg aac agc ttc cac gtg ttc gac cag ggc cag ttt gcc<br>Ser Pro Ser Gly Asn Ser Phe His Val Phe Asp Gln Gly Gln Phe Ala<br>             40                45             50 | 319 |
| aag gag gtg ctg ccc aag tac ttc aag cac aac aac atg gcc agc ttc<br>Lys Glu Val Leu Pro Lys Tyr Phe Lys His Asn Asn Met Ala Ser Phe<br>55                60                65 | 367 |
| gtg cgg cag ctc aac atg tat ggc ttc cgg aaa gtg gtc cac atc gag<br>Val Arg Gln Leu Asn Met Tyr Gly Phe Arg Lys Val Val His Ile Glu<br>70                75                80              85 | 415 |
| cag ggc ggc ctg gtc aag cca gag aga gac gac acg gag ttc cag cac<br>Gln Gly Gly Leu Val Lys Pro Glu Arg Asp Asp Thr Glu Phe Gln His<br>          90                95             100 | 463 |
| cca tgc ttc ctg cgt ggc cag gag cag ctc ctt gag aac atc aag agg<br>Pro Cys Phe Leu Arg Gly Gln Glu Gln Leu Leu Glu Asn Ile Lys Arg<br>         105               110             115 | 511 |
| aaa gtg acc agt gtg tcc acc ctg aag agt gaa gac ata aag atc cgc<br>Lys Val Thr Ser Val Ser Thr Leu Lys Ser Glu Asp Ile Lys Ile Arg<br>          120              125             130 | 559 |
| cag gac agc gtc acc aag ctg ctg acg gac gtg cag ctg atg aag ggg<br>Gln Asp Ser Val Thr Lys Leu Leu Thr Asp Val Gln Leu Met Lys Gly<br>135               140             145 | 607 |
| aag cag gag tgc atg gac tcc aag ctc ctg gcc atg aag cat gag aat<br>Lys Gln Glu Cys Met Asp Ser Lys Leu Leu Ala Met Lys His Glu Asn<br>150             155             160            165 | 655 |
| gag gct ctg tgg cgg gag gtg gcc agc ctt cgg cag aag cat gcc cag<br>Glu Ala Leu Trp Arg Glu Val Ala Ser Leu Arg Gln Lys His Ala Gln<br>         170              175            180 | 703 |
| caa cag aaa gtc gtc aac aag ctc att cag ttc ctg atc tca ctg gtg<br>Gln Gln Lys Val Val Asn Lys Leu Ile Gln Phe Leu Ile Ser Leu Val<br>         185              190           195 | 751 |
| cag tca aac cgg atc ctg ggg gtg aag aga aag atc ccc ctg atg ctg<br>Gln Ser Asn Arg Ile Leu Gly Val Lys Arg Lys Ile Pro Leu Met Leu<br>         200              205           210 | 799 |
| aac gac agt ggc tca gca cat tcc atg ccc aag tat agc cgg cag ttc<br>Asn Asp Ser Gly Ser Ala His Ser Met Pro Lys Tyr Ser Arg Gln Phe<br>215             220              225 | 847 |
| tcc ctg gag cac gtc cac ggc tcg ggc ccc tac tcg gcc ccc tcc cca<br>Ser Leu Glu His Val His Gly Ser Gly Pro Tyr Ser Ala Pro Ser Pro<br>230             235             240            245 | 895 |
| gcc tac agc agc tcc agc ctc tac gcc cct gat gct gtg gcc agc tct<br>Ala Tyr Ser Ser Ser Ser Leu Tyr Ala Pro Asp Ala Val Ala Ser Ser<br>         250              255            260 | 943 |
| gga ccc atc atc tcc gac atc acc gag ctg gct cct gcc agc ccc atg<br>Gly Pro Ile Ile Ser Asp Ile Thr Glu Leu Ala Pro Ala Ser Pro Met<br>         265              270           275 | 991 |
| gcc tcc ccc ggc ggg agc ata gac gag agg ccc cta tcc agc agc ccc<br>Ala Ser Pro Gly Gly Ser Ile Asp Glu Arg Pro Leu Ser Ser Ser Pro<br>         280              285           290 | 1039 |
| ctg gtg cgt gtc aag gag gag ccc ccc agc ccg cct cag agc ccc cgg<br>Leu Val Arg Val Lys Glu Glu Pro Pro Ser Pro Pro Gln Ser Pro Arg<br>295             300             305 | 1087 |
| gta gag gag gcg agt ccc ggg cgc cca tct tcc gtg gac acc ctc ttg<br>Val Glu Glu Ala Ser Pro Gly Arg Pro Ser Ser Val Asp Thr Leu Leu<br>310             315             320           325 | 1135 |

```
tcc ccg acc gcc ctc att gac tcc atc ctg cgg gag agt gaa cct gcc      1183
Ser Pro Thr Ala Leu Ile Asp Ser Ile Leu Arg Glu Ser Glu Pro Ala
            330                 335                 340 ccc gcc tcc gtc aca gcc ctc acg gac gcc agg ggc cac acg gac acc      1231
Pro Ala Ser Val Thr Ala Leu Thr Asp Ala Arg Gly His Thr Asp Thr
        345                 350                 355 gag ggc cgg cct ccc tcc ccc ccg ccc acc tcc acc cct gaa aag tgc      1279
Glu Gly Arg Pro Pro Ser Pro Pro Pro Thr Ser Thr Pro Glu Lys Cys
    360                 365                 370 ctc agc gta gcc tgc ctg gac aag aat gag ctc agt gac cac ttg gat      1327
Leu Ser Val Ala Cys Leu Asp Lys Asn Glu Leu Ser Asp His Leu Asp
375                 380                 385 gct atg gac tcc aac ctg gat aac ctg cag acc atg ctg agc agc cac      1375
Ala Met Asp Ser Asn Leu Asp Asn Leu Gln Thr Met Leu Ser Ser His
390                 395                 400                 405 ggc ttc agc gtg gac acc agt gcc ctg ctg gac ctg ttc agc ccc tcg      1423
Gly Phe Ser Val Asp Thr Ser Ala Leu Leu Asp Leu Phe Ser Pro Ser
                410                 415                 420 gtg acc gtg ccc gac atg agc ctg cct gac ctt gac agc agc ctg gcc      1471
Val Thr Val Pro Asp Met Ser Leu Pro Asp Leu Asp Ser Ser Leu Ala
            425                 430                 435 agt atc caa gag ctc ctg tct ccc cag gag ccc ccc agg cct ccc gag      1519
Ser Ile Gln Glu Leu Leu Ser Pro Gln Glu Pro Pro Arg Pro Pro Glu
        440                 445                 450 gca gag aac agc agc ccg gat tca ggg aag cag ctg gtg cac tac aca      1567
Ala Glu Asn Ser Ser Pro Asp Ser Gly Lys Gln Leu Val His Tyr Thr
    455                 460                 465 gcg cag ccg ctg ttc ctg ctg gac ccc ggc tcc gtg gac acc ggg agc      1615
Ala Gln Pro Leu Phe Leu Leu Asp Pro Gly Ser Val Asp Thr Gly Ser
470                 475                 480                 485 aac gac ctg ccg gtg ctg ttt gag ctg gga gag ggc tcc tac ttc tcc      1663
Asn Asp Leu Pro Val Leu Phe Glu Leu Gly Glu Gly Ser Tyr Phe Ser
                490                 495                 500 gaa ggg gac ggc ttc gcc gag gac ccc acc atc tcc ctg ctg aca ggc      1711
Glu Gly Asp Gly Phe Ala Glu Asp Pro Thr Ile Ser Leu Leu Thr Gly
            505                 510                 515 tcg gag cct ccc aaa gcc aag gac ccc act gtc tcc tagaggcccc          1757
Ser Glu Pro Pro Lys Ala Lys Asp Pro Thr Val Ser
        520                 525 ggaggagctg ggccagccgc ccaccccac ccccagtgca gggctggtct tggggaggca    1817
gggcagcctc gcggtcttgg gcactggtgg gtcggccgcc atagcccag taggacaaac   1877 gggctcgggt ctgggcagca cctctggtca ggagggtcac cctggcctgc cagtctgcct   1937
tcccccaacc ccgtgtcctg tggtttggtt ggggcttcac agccacacct ggactgaccc   1997
tgcaggttgt tcatagtcag aattgtattt tggattttta cacaactgtc ccgttccccg   2057
ctccacagag atacacagat atatacacac agtggatgga cggacaagac aggcagagat   2117
ctataaacag acaggctcta aaaaaaaaaa aaaaaaaa                           2156

<210> SEQ ID NO 2
<211> LENGTH: 529
<212> TYPE: PRT
<213> ORGANISM: Artificial Sequence
<220> FEATURE:
<223> OTHER INFORMATION: Unknown

<400> SEQUENCE: 2

Met Asp Leu Pro Val Gly Pro Gly Ala Ala Gly Pro Ser Asn Val Pro
1               5                   10                  15
```

```
Ala Phe Leu Thr Lys Leu Trp Thr Leu Val Ser Asp Pro Asp Thr Asp
             20                  25                  30

Ala Leu Ile Cys Trp Ser Pro Ser Gly Asn Ser Phe His Val Phe Asp
             35                  40                  45

Gln Gly Gln Phe Ala Lys Glu Val Leu Pro Lys Tyr Phe Lys His Asn
 50                  55                  60

Asn Met Ala Ser Phe Val Arg Gln Leu Asn Met Tyr Gly Phe Arg Lys
 65                  70                  75                  80

Val Val His Ile Glu Gln Gly Leu Val Lys Pro Glu Arg Asp Asp
             85                  90                  95

Thr Glu Phe Gln His Pro Cys Phe Leu Arg Gly Gln Glu Gln Leu Leu
             100                 105                 110

Glu Asn Ile Lys Arg Lys Val Thr Ser Val Ser Thr Leu Lys Ser Glu
             115                 120                 125

Asp Ile Lys Ile Arg Gln Asp Ser Val Thr Lys Leu Leu Thr Asp Val
 130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
             165                 170                 175

Gln Lys His Ala Gln Gln Lys Val Val Asn Lys Leu Ile Gln Phe
             180                 185                 190

Leu Ile Ser Leu Val Gln Ser Asn Arg Ile Leu Gly Val Lys Arg Lys
             195                 200                 205

Ile Pro Leu Met Leu Asn Asp Ser Gly Ser Ala His Ser Met Pro Lys
210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
             245                 250                 255

Ala Val Ala Ser Ser Gly Pro Ile Ile Ser Asp Ile Thr Glu Leu Ala
             260                 265                 270

Pro Ala Ser Pro Met Ala Ser Pro Gly Gly Ser Ile Asp Glu Arg Pro
             275                 280                 285

Leu Ser Ser Ser Pro Leu Val Arg Val Lys Glu Glu Pro Pro Ser Pro
290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
             325                 330                 335

Glu Ser Glu Pro Ala Pro Ala Ser Val Thr Ala Leu Thr Asp Ala Arg
             340                 345                 350

Gly His Thr Asp Thr Glu Gly Arg Pro Pro Ser Pro Pro Pro Thr Ser
             355                 360                 365

Thr Pro Glu Lys Cys Leu Ser Val Ala Cys Leu Asp Lys Asn Glu Leu
             370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
             405                 410                 415

Leu Phe Ser Pro Ser Val Thr Val Pro Asp Met Ser Leu Pro Asp Leu
             420                 425                 430
```

-continued

```
Asp Ser Ser Leu Ala Ser Ile Gln Glu Leu Leu Ser Pro Gln Glu Pro
        435                 440                 445

Pro Arg Pro Pro Glu Ala Glu Asn Ser Ser Pro Asp Ser Gly Lys Gln
    450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
        515                 520                 525

Ser

<210> SEQ ID NO 3
<211> LENGTH: 15
<212> TYPE: DNA
<213> ORGANISM: Artificial Sequence
<220> FEATURE:
<223> OTHER INFORMATION: Other Nucleic Acid
<220> FEATURE:
<221> NAME/KEY: misc_feature
<222> LOCATION: (1)...(15)
<223> OTHER INFORMATION: n = A,T,C or G

<400> SEQUENCE: 3
ngaannttcn ngaan                                                    15
```